United States Patent
Contorni et al.

(10) Patent No.: US 11,246,921 B2
(45) Date of Patent: *Feb. 15, 2022

(54) INFLUENZA VACCINES WITH REDUCED AMOUNTS OF SQUALENE

(71) Applicant: Seqirus UK Limited, Berkshire (GB)

(72) Inventors: Mario Contorni, Siena (IT); Derek O'Hagan, Cambridge, MA (US); Nicola Groth, Buonconvento (IT)

(73) Assignee: Seqirus UK Limited, Berkshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/452,783

(22) Filed: Jun. 26, 2019

(65) Prior Publication Data

US 2020/0155664 A1 May 21, 2020

Related U.S. Application Data

(63) Continuation of application No. 16/178,897, filed on Nov. 2, 2018, now abandoned, which is a continuation of application No. 15/007,719, filed on Jan. 27, 2016, now Pat. No. 10,149,901, which is a continuation of application No. 13/148,939, filed as application No. PCT/IB2010/000312 on Feb. 10, 2010, now Pat. No. 9,278,126.

(60) Provisional application No. 61/207,385, filed on Feb. 10, 2009.

(51) Int. Cl.
*A61K 39/145* (2006.01)
*C12N 7/00* (2006.01)
*A61K 39/12* (2006.01)
*A61K 39/00* (2006.01)

(52) U.S. Cl.
CPC ............ *A61K 39/145* (2013.01); *A61K 39/12* (2013.01); *C12N 7/00* (2013.01); *A61K 2039/545* (2013.01); *A61K 2039/55566* (2013.01); *A61K 2039/70* (2013.01); *C12N 2760/16134* (2013.01); *C12N 2760/16234* (2013.01)

(58) Field of Classification Search
CPC ........ A61K 39/145; A61K 2039/55566; A61K 2039/70; A61K 47/06; A61K 9/1075; A61P 31/16; A61P 37/04; A61P 39/00; A61P 31/04
See application file for complete search history.

(56) References Cited

U.S. PATENT DOCUMENTS

| | | | |
|---|---|---|---|
| 4,500,513 A | 2/1985 | Brown et al. |
| 5,162,112 A | 11/1992 | Oxford et al. |
| 5,580,767 A | 12/1996 | Cowsert et al. |
| 5,750,110 A | 5/1998 | Prieels et al. |
| 5,762,939 A | 6/1998 | Smith et al. |
| 5,776,468 A | 7/1998 | Hauser |
| 5,824,536 A | 10/1998 | Webster et al. |
| 5,948,410 A | 9/1999 | Van Scharrenburg et al. |
| 6,136,321 A | 10/2000 | Barrett et al. |
| 6,245,532 B1 | 6/2001 | Smith et al. |
| 6,299,884 B1 | 10/2001 | Van Nest et al. |
| 6,334,856 B1 | 1/2002 | Allen et al. |
| 6,372,223 B1 | 4/2002 | Kistner et al. |
| 6,372,227 B1 | 4/2002 | Garcon et al. |
| 6,451,325 B1 | 9/2002 | Van Nest et al. |
| 6,506,386 B1 | 1/2003 | Friede et al. |
| 6,544,518 B1 | 4/2003 | Friede et al. |
| 6,861,410 B1 | 3/2005 | Ott et al. |
| 6,869,607 B1 | 3/2005 | Buschle et al. |
| 6,951,754 B2 | 10/2005 | Hoffmann |
| 7,316,813 B2 | 1/2008 | Eichhorn |
| 7,357,936 B1 | 4/2008 | Garcon |
| 7,384,642 B2 | 6/2008 | Minke et al. |
| 7,425,336 B2 | 9/2008 | Minke et al. |
| 7,566,458 B2 | 7/2009 | Yang et al. |
| 7,588,774 B2 | 9/2009 | Campbell et al. |
| 7,641,911 B2 | 1/2010 | Ott et al. |
| 7,959,931 B2 | 6/2011 | Colegate et al. |
| 8,206,749 B1 | 6/2012 | O'Hagan et al. |
| 8,309,139 B2 | 11/2012 | O'Hagan et al. |
| 8,506,966 B2 | 8/2013 | Podda et al. |

(Continued)

FOREIGN PATENT DOCUMENTS

| | | |
|---|---|---|
| CA | 1122527 | 4/1982 |
| CA | 2235257 | 4/1997 |

(Continued)

OTHER PUBLICATIONS

Advisory Action dated Apr. 30, 2014, for U.S. Appl. No. 12/448,057, filed Dec. 5, 2007, 4 pages.

(Continued)

*Primary Examiner* — Bao Q Li
(74) *Attorney, Agent, or Firm* — Finnegan, Henderson, Farabow, Garrett & Dunner, LLP

(57) ABSTRACT

Influenza vaccines include hemagglutinin from at least one influenza A virus strain and at least one influenza B virus strain. They also include an oil-in-water emulsion adjuvant with submicron oil droplets, comprising squalene. In some embodiments the hemagglutinin concentration is >12 µg/ml per strain. In some embodiments the squalene concentration is <19 mg/ml. In some embodiments the vaccine is mercury-free. In some embodiments the vaccine has a unit dose volume between 0.2-0.3 mL. In some embodiments the squalene concentration is 9.75 mg/mL or 4.88 mg/mL. In some embodiments the vaccine includes antigens from two influenza A virus strains and two influenza B virus strains.

20 Claims, No Drawings

(56) References Cited

U.S. PATENT DOCUMENTS

| | | |
|---|---|---|
| 8,808,686 B2 | 8/2014 | Del Giudice et al. |
| 8,895,629 B2 | 11/2014 | Rueckl et al. |
| 9,278,126 B2 * | 3/2016 | Contorni ............ A61K 39/145 |
| 9,566,326 B2 | 2/2017 | Podda et al. |
| 10,149,901 B2 * | 12/2018 | Contorni ................ C12N 7/00 |
| 2003/0147898 A1 | 8/2003 | Van Nest et al. |
| 2004/0071734 A1 | 4/2004 | Garcon et al. |
| 2004/0081686 A1 | 4/2004 | Kravtzoff et al. |
| 2004/0096463 A1 | 5/2004 | Garcon et al. |
| 2004/0109874 A1 | 6/2004 | Chen et al. |
| 2004/0223976 A1 | 11/2004 | Bianchi et al. |
| 2004/0241187 A1 | 12/2004 | Eichhorn |
| 2005/0123550 A1 | 6/2005 | Laurent et al. |
| 2005/0123599 A1 | 6/2005 | Ott et al. |
| 2005/0186621 A1 | 8/2005 | Galarza et al. |
| 2005/0220854 A1 | 10/2005 | Maa et al. |
| 2005/0255121 A1 | 11/2005 | Campbell et al. |
| 2005/0287172 A1 | 12/2005 | Yang et al. |
| 2006/0115489 A1 | 6/2006 | Birkett et al. |
| 2006/0147477 A1 | 7/2006 | Cabezon Siliva et al. |
| 2006/0188977 A1 | 8/2006 | Schwartz |
| 2006/0211644 A1 | 9/2006 | Krieg et al. |
| 2006/0263386 A1 | 11/2006 | Buschle et al. |
| 2007/0048819 A1 | 3/2007 | Minke et al. |
| 2007/0048821 A1 | 3/2007 | Minke et al. |
| 2007/0116709 A1 | 5/2007 | O'Hagan et al. |
| 2007/0141078 A1 | 6/2007 | D'Hondt et al. |
| 2007/0298093 A1 | 12/2007 | Konur et al. |
| 2008/0181911 A1 | 7/2008 | Hanon et al. |
| 2008/0254065 A1 | 10/2008 | Podda et al. |
| 2009/0060950 A1 | 3/2009 | Kistner et al. |
| 2009/0202590 A1 | 8/2009 | Colegate et al. |
| 2009/0220545 A1 | 9/2009 | Del Giudice et al. |
| 2009/0220546 A1 | 9/2009 | Podda et al. |
| 2010/0010199 A1 | 1/2010 | Tsai et al. |
| 2010/0189741 A1 | 7/2010 | Ballou et al. |
| 2010/0322969 A1 | 12/2010 | Jin et al. |
| 2011/0045022 A1 | 2/2011 | Tsai |
| 2012/0027813 A1 | 2/2012 | Podda et al. |
| 2012/0093860 A1 | 4/2012 | Stohr et al. |
| 2013/0004942 A1 | 1/2013 | Stohr et al. |
| 2013/0273104 A1 | 10/2013 | Podda et al. |
| 2015/0174234 A1 | 6/2015 | Contorni |
| 2017/0202955 A1 | 7/2017 | Podda et al. |

FOREIGN PATENT DOCUMENTS

| | | |
|---|---|---|
| EP | 0 864 646 A2 | 9/1998 |
| GB | 0506001.7 | 3/2005 |
| JP | 62201573 A | 9/1987 |
| JP | 2003523310 A | 8/2003 |
| WO | WO 90/14837 | 12/1990 |
| WO | WO 95/17209 | 6/1995 |
| WO | WO 95/17210 | 6/1995 |
| WO | WO 96/15231 | 5/1996 |
| WO | WO 96/33739 | 10/1996 |
| WO | WO 97/14434 | 4/1997 |
| WO | WO 97/37000 | 10/1997 |
| WO | WO 97/37001 | 10/1997 |
| WO | WO 97/38094 A1 | 10/1997 |
| WO | WO 98/15287 | 4/1998 |
| WO | WO 98/16247 | 4/1998 |
| WO | WO 98/40100 | 9/1998 |
| WO | WO 98/56414 | 12/1998 |
| WO | WO 98/57659 | 12/1998 |
| WO | WO 98/57660 | 12/1998 |
| WO | WO 99/11241 | 3/1999 |
| WO | WO 99/27961 | 6/1999 |
| WO | WO 00/15251 | 3/2000 |
| WO | WO 00/60050 | 10/2000 |
| WO | WO 00/62800 | 10/2000 |
| WO | WO 01/04333 A1 | 1/2001 |
| WO | WO 01/21151 A1 | 3/2001 |
| WO | WO 01/21152 A1 | 3/2001 |
| WO | WO 01/21207 A2 | 3/2001 |
| WO | WO 01/22992 A2 | 4/2001 |
| WO | WO 01/80836 | 11/2001 |
| WO | WO 02/32450 A2 | 4/2002 |
| WO | WO 02/32454 A1 | 4/2002 |
| WO | WO 02/074336 | 9/2002 |
| WO | WO 02/085446 | 10/2002 |
| WO | WO 02/097072 A2 | 12/2002 |
| WO | WO 03/002069 | 1/2003 |
| WO | WO 03/076601 A1 | 9/2003 |
| WO | WO 2004/058142 A2 | 7/2004 |
| WO | WO 2004/075829 | 9/2004 |
| WO | WO 2004/084937 | 10/2004 |
| WO | WO 2004/098509 | 11/2004 |
| WO | WO 2005/009462 A2 | 2/2005 |
| WO | WO 2005/107797 A1 | 11/2005 |
| WO | WO 2005/113756 A1 | 12/2005 |
| WO | WO 2005/117958 | 12/2005 |
| WO | WO 2006/060710 | 6/2006 |
| WO | WO 2006/098901 A2 | 9/2006 |
| WO | WO 2006/100109 A1 | 9/2006 |
| WO | WO 2006/100110 A1 | 9/2006 |
| WO | WO 2006/100111 A1 | 9/2006 |
| WO | WO 2007/006939 | 1/2007 |
| WO | WO 2007/045674 A1 | 4/2007 |
| WO | WO 2007/052057 A2 | 5/2007 |
| WO | WO 2007/052058 A1 | 5/2007 |
| WO | WO 2007/052059 A2 | 5/2007 |
| WO | WO 2007/052061 A2 | 5/2007 |
| WO | WO 2007/052155 A2 | 5/2007 |
| WO | WO 2007/110776 A1 | 10/2007 |
| WO | WO 2008/032219 A2 | 3/2008 |
| WO | WO 2008/043774 A1 | 4/2008 |
| WO | WO 2008/068631 A2 | 6/2008 |
| WO | WO 2008/128939 A1 | 10/2008 |

OTHER PUBLICATIONS

Altaner et al., "Envelope glycoprotein gp51 of bovine leukemia virus is differently glycosylated in cells of various species and organ origin", Vet Immunol Immunopathol, 36(2):163-177, (1993).

Alymova et al. (1998) "Immunogenicity and protective efficacy in mice of influenza B virus vaccines grown in mammalian cells or embryonated chicken eggs" *J Virol*, 72(5):4472-7.

Anderson et al., "Physicochemical characterization and biological activity of synthetic TLR4 agonist formulations," Colloids Surf B Biointerfaces, 75(1):123-132, (2010).

Arora et al., "Micro-scale devices for transdermal drug delivery", *Int J Pharm*, 364(2):227-36, (2008).

Assessment Report for Celvapan, Doc. Ref: EMEA/CHMP/629184/2009, (2009).

Babiuk et al., "Aggregate content influences the Th1/Th2 immune response to influenza vaccine: evidence from a mouse model," J Med Virol, 72(1):138-142, (2004).

Bandell et al., "Protective efficacy of live-attenuated influenza vaccine (multivalent, Ann Arbor strain): a literature review addressing interference," Expert Rev Vaccines, 10(8):1131-1141, (2011).

Barr et al. (2003) "Reassortants in recent human influenza A and B isolates from South East Asia and Oceania" *Vir Res*, 98:35-44.

Barr et al. (2006) "Circulation and antigenic drift in human influenza B viruses in SE Asia and Oceania since 2000" *Commun Dis Intell Q Rep*, 30(3):350-7.

De Barros Jr. et al., "Characterization of sialidase from an influenza A (H3N2) virus strain: kinetic parameters and substrate specificity," Intervirology, 46(4):199-206, (2003).

BASF, "Pluronic L121 BlocK Copolymer Surfactant, Technical Bulletin", 1 page, (2004).

Baudner et al., "MF59 emulsion is an effective delivery system for a synthetic TLR4 agonist (E6020)," Pharm Res, 26(6):1477-1485, (2009).

Belshe et al., "Safety, efficacy, and effectiveness of cold-adapted, live, attenuated, trivalent, intranasal influenza vaccine in adults and children", *Philos Trans R Soc Lond B Biol Sci*, 356(1416):1947-51, (2001).

Beran et al. (2013) "Immunogenicity and safety of quadrivalent versus trivalent inactivated influenza vaccine: a randomized, controlled trial in adults" *BMC Infect Dis*, 13:224.

(56) References Cited

OTHER PUBLICATIONS

Berger, "Science commentary: Th1 and Th2 responses: what are they?", BMJ, 321 (7258):424, (2000).
Biere et al. (2010) "Differentiation of influenza B virus lineages Yamagata and Victoria by realtime PCR" *J Clin Microbiol*, 48(4):1425-7.
Bordi et al., "Salt-induced aggregation in cationic liposome aqueous suspensions resulting in multi-step self-assembling complexes," Colloids and Surfaces B: Biointerfaces, 26(4):341-350, (2002).
Bresson et al., "Safety and immunogenicity of an inactivated split-virion influenza/Vietnam/1194/2004 (H5N1) vaccine: phase I randomised trial", Lancet 367(9523):1657-1664, (2006).
Brühl et al., "Humoral and cell-mediated immunity to Vero cell-derived influenza vaccine", Vaccine, 19(9-10):1149-1158, (2000).
Canada Communicable Disease Report, vol. 27 (ACS-4), (2001).
Carmona et al., "Immunogenicity and safety of AS03-adjuvanted 2009 influenza A H1N1 vaccine in children 6-35 months", *Vaccine*, 28(36):5837-44, (2010).
Centers for Disease Control and Prevention, *MMWR*, 56:1-53, (2007).
CenterWatch published by FDA (Fluad New FDA Drug Approval copyright 1995-2016, pp. 1-2), searched by 2016.
Chaloupka et al. (1996) "Comparative analysis of six European influenza vaccines" *Eur J Clin Microbial Infect Dis*, 15(2):121-7.
Chan et al. (2004) "Phylogenetic analysis of influenza B virus in Taiwan, 1997 to 2001" *J Microbial Immunol Infect*, 37(3):135-44.
Chattaraj et al., "Biodegradable microparticles of influenza viral vaccine: comparison of the effects of routes of administration on the in vivo immune response in mice," J Control Release, 58(2):223-232, (1999).
ChemBlink at www.chemblink.com, 2 pages, 2010.
Chen et al., "Epidermal powder immunization: cellular and molecular mechanisms for enhancing vaccine immunogenicity", *Virus Res*, 103(1-2):147-53, (2004).
Chen et al., "Serum and mucosal immune responses to an inactivated influenza virus vaccine induced by epidermal powder immunization", *J Virol*, 75(17):7956-65, (2001).
Clegg et al., "Adjuvant solution for pandemic influenza vaccine production," Proc Natl Acad Sci U S A, 109(43):17585-17590, (2012).
Committee for Proprietary Medical Products, "Note for guidance on harmonization of requirements for influenza vaccines", *PMP/BWP* 214/96 1-18, (1997).
Cooper et al., "Safety and immunogenicity of CPG 7909 injection as an adjuvant to Flurix influenza vaccine", Vaccine, 22(23-24):3136-3143, (2004).
Cormier et al., "Macroflux technology for transdermal delivery of therapeutic proteins and vaccines", *Drugs and the Pharmaceutical Sciences*, 126:589-598, (2003).
Cormier et al., "Transdermal delivery of desmopressin using a coated microneedle array patch system", *J Control Release*, 97(3):503-11, (2004).
Couch et al., "Superior antigen-specific CD4+ T-cell response with AS03-adjuvantation of a trivalent influenza vaccine in a randomised trial of adults aged 65 and older", BMC Infect Dis, 14:425, (2014).
Daems et al., "Anticipating crisis: towards a pandemic flu vaccination strategy through alignment of public health and industrial policy", Vaccine, 23(50):5732-5742, (2005).
Danihelkova et al., "Disruption of influenza virus A by diethylether-Tween and tri-N-butyl phosphate-Tween mixtures", Acta Virol 28:26-32, (1984).
Dapat et al. (2012) "Genetic characterization of human influenza viruses in the pandemic (2009-2010) and post-pandemic (2010-2011) periods in Japan" *PLoS One*, 7(6):e36455.
Della Cioppa et al. (2011) "Trivalent and quadrivalent MF59®-adjuvanted influenza vaccine in young children: A dose- and schedule-finding study" *Vaccine*, 29:8696-8704.
Demicheli et al., "The Cochrane collaboration: Vaccines for preventing influenza in healthy children (Review)", *The Cochrane library*, Issue 3, (2006).

Dooley et al., "Adjuvanted Influenza Vaccine," BioDrugs, 14(1):61-69, (2000).
ECDC, "Technical report on the scientific panel on Vaccines and immunization: Infant and children seasonal immunization against influenza on a routine basis during inter-pandemic period", Stockholm, (2007).
Eickhoff (2006) "The 2005 to 2006 influenza season is over" *Infectious Disease News*, 3 pages.
EMEA (Jan. 2002) "Cell Culture Inactivated Influenza Vaccines" 7 pages.
English Translation of Japanese Notice of Reasons for Rejection dated Dec. 19, 2011, for Japanese Application No. 2008-538453, 8 pages.
Esposito et al., "Influenza A/H1N1 MF59-adjuvanted vaccine in preterm and term children aged 6 to 23 months", *Pediatrics*, 127(5):e1161-8, (2011).
European Medicines Agency, "Celvapan, International nonproprietary name: Pandemic influenza vaccine (H5N1) (whole virion, vero cell derived, inactivated)", Assessment Report, pp. 1-11, (2009).
European Medicines Agency, "Pumarix, Common name: Pandemic influenza vaccine (H5N1) (split viron, inactivated, adjuvated)", Assessment Report, pp. 1-75, (2011).
European Search Report, dated Mar. 14, 2013, for European Application No. 11162713.9, 6 pages.
Evans et al., "Enhancement of antigen-specific immunity via the TLR4 ligands MPL adjuvant and Ribi.529," Expert Rev Vaccines, 2(2):219-229, (2003).
FDA News Release (Feb. 29, 2012) "FDA approves first quadrivalent vaccine to prevent seasonal influenza" 2 pages.
Fedson, "Preparing for pandemic vaccination: an international policy agenda for vaccine development," J Public Health Policy, 26(1):4-29, (2005).
Ferguson et al., "Ecological and immunological determinants of influenza evolution", *Nature*, 422(6930):428-33, (2003).
Final Office Action dated Jun. 7, 2013, for U.S. Appl. No. 12/448,057, filed Dec. 5, 2007, 12 pages.
Final Office Action dated Jan. 3, 2014, for U.S. Appl. No. 12/448,057, filed Dec. 5, 2007, 15 pages.
Final Office Action dated Jun. 24, 2015, for U.S. Appl. No. 12/448,057, filed Dec. 5, 2007, 13 pages.
Final Office Action, dated Jun. 16, 2015, for U.S. Appl. No. 14/035,668, filed Sep. 24, 2013, 17 pages.
FLUAD product information (2005) "Summary of Product Characteristics" Biogenetech / Novartis, 4 pages.
Fox, C. (2009) "Squalene emulsions for parenteral vaccine and drug delivery" *Molecules*, 14(9):3286-312.
Frey et al. (2003) "Comparison of the safety, tolerability, and immunogenicity of a MF59-adjuvanted influenza vaccine and a non-adjuvanted influenza vaccine in non-elderly adults" *Vaccine*, 21(27-30):4234-7.
Fukuda et al., "Inactivated Influenza Vaccines", in Vaccines, Plotkin & Orenstein, eds., Chapters 17 and 18, pp. 339-388, (2004).
Galarza et al., "Virus-like particle (VLP) vaccine conferred complete protection against a lethal influenza virus challenge," Viral Immunol, 18(2):365-372, (2005).
Gambaryan et al., "Effects of host-dependent glycosylation of hemagglutinin on receptor-binding properties on H1N1 human influenza A virus grown in MDCK cells and in embryonated eggs", Virology, 247(2):170-177, (1998).
Garcia-Sicilia et al., "Immunogenicity and safety of AS03-adjuvanted H1N1 pandemic vaccines in children and adolescents", *Vaccine*, 29(26):4353-61, (2011).
Garçon et al., "Development and evaluation of AS03, an Adjuvant System containing α-tocopherol and squalene in an oil-in-water emulsion", *Expert Rev Vaccines*, 11(3):349-66, (2012).
Geier et al., "Influenza vaccination and Guillain Barre syndrome", Clin Immunol, 107(2):116-121, (2003).
Ghendon et al., "The effect of mass influenza immunization in children on the morbidity of the unvaccinated elderly", *Epidemiol Infect*, 134(1):71-8, (2006).
Gilca et al., "Effectiveness of pandemic H1N1 vaccine against influenza-related hospitalization in children", *Pediatrics*, 128(5):e1084-91, (2011).

(56) References Cited

OTHER PUBLICATIONS

Goldblatt, "Conjugate vaccines" *Clin Exp Immunol*, 119(1):1-3, (2000).
Gonzalez et al., "Safety and immunogenicity of a paediatric presentation of an influenza vaccine," Arch Dis Child, 83(6):488-491, (2000).
Govaert et al. (1994) "Immune response to influenza vaccination of elderly people. A randomized double-blind placebo-controlled trial" *Vaccine*, 12(13):1185-9.
Govaert et al. (1994) "The efficacy of influenza vaccination in elderly individuals. A randomized double-blind placebo-controlled trial" *JAMA*, 272(21):1661-5.
Govorkova et al. (1999) "Growth and immunogenicity of influenza viruses cultivated in Vero or MDCK cells and in embryonated chicken eggs" *Dev Biol Stand*, 98:39-51; discussion 73-4.
Govorkova et al. (1999) "Selection of receptor-binding variants of human influenza A and B viruses in baby hamster kidney cells" *Virology*, 262(1):31-8.
Halperin et al., "A comparison of the intradermal and subcutaneous routes of influenza vaccination with A/New Jersey/76 (swine flu) and A/Victoria/75: report of a study and review of the literature", *AJPH*, 69(12):1247-51, (1979).
Halperin et al., "Safety and immunogenicity of a new influenza vaccine grown in mammalian cell culture," Vaccine, 16(13):1331-1335, (1998).
Halperin et al., "Safety and immunogenicity of a trivalent, inactivated, mammalian cell culture-derived influenza vaccine in healthy adults, seniors, and children," Vaccine, 20(7-8):1240-1247, (2002).
Hauge et al., "The immunogenicity of a cell-derived H7N1 split influenza virion vaccine in mice," Scand J Immunol, 69(6):576-578, (2009).
He et al., "Calcium phosphate nanoparticle adjuvant", Clin Diagn Lab Immunol, 7(6):899-903, (2000).
Health Canada, Health Products and Food Branch, "AREPANRIX™ H1N1, AS03-Adjuvated H1N1 Pandemic Influenza Vaccine," Summary basis of decision (SBD), pp. 1-14, (2010).
Hehme et al., "Ten years of experience with the trivalent split-influenza vaccine, Fluarix TM", *Clin Drug Invest*, 22(11):751-69, (2002).
Hehme et al., "Immunogenicity of a monovalent, aluminum-adjuvanted influenza whole virus vaccine for pandemic use", Virus Res, 103(1-2):163-171, (2004).
Heikkinen et al., "Burden of influenza in children in the community", *J Infect Dis*, 190(8):1369-73, (2004).
Herbinger et al. (2014) "A phase II study of an investigational tetravalent influenza vaccine formulation combining MF59®: adjuvanted, pre-pandemic, A/H5N1 vaccine and trivalent seasonal influenza vaccine in healthy adults" *Hum Vaccin Immunother*, 10(1):92-9.
Higgins et al., "MF59 adjuvant enhances the immunogenicity of influenza vaccine in both young and old mice," Vaccine, 14(6):478-484, (1996).
Hiromoto et al. (2000) "Phylogenetic analysis of the three polymerase genes (PB1, PB2 and PA) of influenza B virus" *J Gen Virol*, 81 (Pt 4):929-37.
Horimoto and Kawaoka, "Influenza: Lessons from past pandemics, warnings from current incidents", Nat Rev Microbiol 3(8):591-600, (2005).
Ichinohe et al., "Synthetic double-stranded RNA poly(I:C) combined with mucosal vaccine protects against influenza virus infection," J Virol, 79(5):2910-2919, (2005).
International Search Report for PCT/IB2010/000312, dated Nov. 18, 2010, 7 pages.
Iskander et al., "The burden of influenza in children", *Curr Opin Infect Dis*, 20(3):259-63, (2007).
Izurieta et al., "Influenza and the rates of hospitalization for respiratory disease among infants and young children", *N Engl J Med*, 342(4):232-9, (2000).

Jefferson et al., "Vaccines for preventing influenza in healthy children (Review)" The Cochrane Collaboration, published by John Wiley & Sons, Ltd., (2008).
Jefferson et al. (2008) "Vaccines for preventing influenza in healthy children" *Cochrane Database Syst Rev*, (2):CD004879, Published by JohnWiley & Sons, Ltd.
Jefferson et al. (2010) "Vaccines for preventing influenza in the elderly" *Cochrane Database Syst Rev*, 17(2):CD004876.
Johannsen et al., "The quantification of the haemagglutinin content of influenza whole virus and Tween-ether split vaccines", J Biol Stand, 11(4):341-352, (1983).
Joseph et al., "Liposomal immunostimulatory DNA sequence (ISS-ODN): an efficient parenteral and mucosal adjuvant for influenza and hepatitis B vaccines", Vaccine, 20(27-28):3342-3354, (2002).
Kashiwagi, S. (Nov. 15, 1999) "Measures against influenza. Influenza and vaccine" *JIM*, 9(11):971-974.
Kasturi et al., "Programming the magnitude and persistence of antibody responses with innate immunity," Nature, 470(7335):543-547, (2011).
Kishida et al. (2012) "Evaluation of influenza virus A/H3N2 and B vaccines on the basis of cross-reactivity of postvaccination human serum antibodies against influenza viruses A/H3N2 and B isolated in MDCK cells and embryonated hen eggs" *Clin Vaccine Immunol*, 19(6):897-908.
Kistner et al., "A whole virus pandemic influenza H1N1 vaccine is highly immunogenic and protective in active immunization and passive protection mouse models," PLoS One, 5(2):e9349, (2010).
Klang et al., "The stability of piroxicam incorporated in a positively-charged submicron emulsion for ocular administration", International Journal of Pharmaceutics, 132:33-44, (1996).
Klinman, "Immunotherapeutic uses of CpG oligodeoxynucleotides," Nat Rev Immunol, 4(4):249-258, (2004).
Knipe et al., "Orthomyxoviridae: The Viruses and Their Replication" in Fields Virology, $4^{th}$ Edition, Ch. 46, pp. 1487-1531, (2004).
Koelle et al., "Epochal evolution shapes the phylodynamics of interpandemic influenza A (H3N2) in humans", *Science* 314(5807):1898-903, (2006).
Kommareddy et al., "Influenza subunit vaccine coated microneedle patches elicit comparable immune responses to intramuscular injection in guinea pigs", *Vaccine*, 31(34):3435-41, (2013).
Koutsonanos et al., Additional Data, Submitted on Jul. 30, 2014 during prosecution for EP1807116, 4 pages.
Krieg, "CpG motifs: the active ingredient in bacterial extracts?" Nat Med, 9(7):831-835, (2003).
Kumagai et al., "Poor immune responses to influenza vaccination in infants", *Vaccine*, 22(25-26):3404-10, (2004).
Kurashige, T. and Tomoda, T. (Feb. 2000) "Prevention of influenza by vaccination" *Sogo Rinsho (General Clinical)*, 49(2):285-288.
Latebreaking Abstracts: Late Breaker Poster, Intradermal 2009 Pandemic Influenza A (H1N1) Vaccination as as a Strategy for Dose and Adjuvant Sparing, 3 pages, (2010).
Lazar et al., "Cell-mediated immune response of human lymphocytes to influenza A/USSR (H1N1) virus infection", *Infect Immun*, 27(3):867-71, (1980).
Levandowski et al. (1991) "Antibody responses to influenza B viruses in immunologically unprimed children" *Pediatrics*, 88(5):1031-6.
Lin et al. (2004) "Recent changes among human influenza viruses" *Vir Res* 103:47-52.
Lin et al., "Different immunity elicited by recombinant H5N1 hemagglutinin proteins containing pauci-mannose, high-mannose, or complex type N-glycans", PLoS One, 8(6):e66719, (2013).
Lindblad, "Aluminum compounds for use in vaccines", Immunol Cell Biol, 82(5):497-505, (2004).
Lopez (2013) "Combined administration of MF59-adjuvanted A/H5N1 prepandemic and seasonal influenza vaccines: long-term antibody persistence and robust booster responses 1 year after a one-dose priming schedule" *Clin Vaccine Immunol*, 20(5):753-8.
Lopez et al. (2011) "Combined, concurrent, and sequential administration of seasonal influenza and MF59-adjuvanted A/H5N1 vaccines: a phase II randomized, controlled trial of immunogenicity and safety in healthy adults" *J Infect Dis*, 203(12):1719-28.
Louie et al., *Pediatrics*, 117(4):e610-8, (2006).

(56) References Cited

OTHER PUBLICATIONS

Maa et al., "Influenza vaccine powder formulation development: spray-freeze-drying and stability evaluation", *J Pharm Sci*, 93(7):1912-23, (2004).
Macroflux transdermal technology development for the delivery of therapeutic peptides and proteins, *Drug Delivery Technology*, 2(5), (2002).
Maeda et al., "Failure of inactivated influenza A vaccine to protect healthy children aged 6-24 months," Pediatr Int, 46(2):122-125, (2004).
Marsland et al., "Allergic airway inflammation is exacerbated during acute influenza infection and correlates with increased allergen presentation and recruitment of allergen-specific T-helper type 2 cells", Clin Exp Allergy, 34(8):1299-1306, (2004).
Matriano et al., "Macroflux microprojection array patch technology: a new and efficient approach for intracutaneous immunization", *Pharm Res*, 19(1):63-70, (2002).
McCullers et al. (1999) "Reassortment and insertion-deletion are strategies for the evolution of influenza B viruses in nature" *J Virol*, 73(9):7343-8.
McEwen et al., "Synthetic recombinant vaccine expressing influenza haemagglutinin epitope in *Salmonella flagellin* leads to partial protection in mice," Vaccine, 10(6):405-411, (1992).
MedImmune (Feb. 29, 2012) "MedImmune Announces FDA Approval of First Four-strain Flu Vaccine, Flu Mist® Quadrivalent (Influenza Vaccine Live, Intranasal)" 3 pages.
Meijer et al. (2006) "Euroroundup: Epidemiological and virological assessment of influenza activity in Europe, during the 2004-2005 winter" *Eurosurveillance*, vol. 11, Issue 5, 16 pages.
Minutello et al. (1999) "Safety and immunogenicity of an inactivated subunit influenza virus vaccine combined with MF59 adjuvant emulsion in elderly subjects, immunized for three consecutive influenza seasons" *Vaccine*, 17:99-104.
Mitchell et al., "Immunogenicity and safety of inactivated influenza virus vaccine in young children in 2003-2004", *Pediatr Infect Dis J*, 24(10):925-7, (2005).
Mitragotri, "Immunization without needles", *Nat Rev Immunol*, 5(12):905-16, (2005).
Mikszta et al., "Improved genetic immunization via micromechanical disruption of skin-barrier function and targeted epidermal delivery", *Nat Med*, 8(4):415-9, (2002).
Moldoveanu et al., "CpG DNA, a novel immune enhancer for systemic and mucosal immunization with influenza virus," Vaccine, 16(11-12):1216-1224, (1998).
Moran et al., "Th2 Responses to Inactivated Influenza Virus Can Be Converted to Th1 Responses and Facilitate Recovery from Heterosubtypic Virus Infection," The Journal of Infectious Diseases, 180:579-585, (1999).
Morio et al. (1994) "Three year follow up study of national influenza vaccination practices in Japan" *J Epidemiol Community Health*, 48(1):46-51.
Neirynck et al., "A universal influenza A vaccine based on the extracellular domain of the M2 protein", Nat Med, 5(10):1157-1163, (1999).
Neuzil et al., "The effect of influenza on hospitalizations, outpatient visits, and courses of antibiotics in children", *N Engl J Med*, 27:342(4):225-231, (2000).
Nicholson et al., "Safety and antigenicity of non-adjuvanted and MF59-adjuvanted influenza A/Duck/Singapore/97 (H5N3) vaccine: a randomized trial of two potential vaccines against H5N1 influenza," Lancet, 16:357(9272):1937-1943, (2001).
Nony et al., "Impact of osmolality on burning sensations during and immediately after intramuscular injection of 0.5 ml of vaccine suspensions in healthy adults", Vaccine, 19(27):3645-3651, (2001).
Notice of Opposition, filed in opposition against EP2121011, dated Feb. 20, 2015, 41 pages.
Notice of Opposition against European Patent No. EP 2 396 032, filed Jun. 28, 2017.

Novartis Vaccines and Diagnostics (Aug. 2009). "FCC H1 N1sw Vaccine, Module 2," Retrieved Jul. 16, 2014 from <http://www.mhlw.go.jp/shingi/2010/01 /dl/s0115-7z.pdb>.
Novartis International AG, "Novartis Phase III study indicates MF59® adjuvanted influenza vaccine, Fluad®, is 75 percent more efficacious than studied non-adjuvanted vaccines in young children", Novartis Media Release, 4 pages, (2010).
Novartis Press Release (Jun. 13, 2007) "Novartis Gains European Approval for Its Innovative Flu Vaccine Optflu" 3 pages.
Nyerges et al., "Sensitizing activity to egg protein of an A1PO4-adjuvated full-virus influenza vaccine", Acta Microbial Acad Sci Hung, 29(4): 245-253, (1982).
O'Hagan, "Vaccine Adjuvants: Preparation Methods and Research Protocols", Humana Press, pp. 211-228 (2000).
O'Hagan et al., "Synergistic adjuvant activity of immunostimulatory DNA and oil/water emulsions for immunization with HIV p55 gag antigen," Vaccine, 20(27-28):3389-3398, (2002).
O'Hagan et al., "Microparticles as vaccine adjuvants and delivery systems," Expert Rev Vaccines, 2(2):269-283, (2003).
O'Hagan et al., "Novel approaches to vaccine delivery", Pharma Res 21(9):1519-1530, (2004).
O'Hagan. (2007) "MF59 is a safe and potent vaccine that enhances protection against influenza virus infection" *Expert Rev Vaccines*, 6(5):699-710.
O'Hagan et al. (2008) "MF59: A safe and potent oil in water emulsion adjuvant for influenza vaccines, which induces enhanced protection against virus challenge" *Influenza Vaccines for the Future*, pp. 221-244.
O'Hagan et al., "MF59 adjuvant: the best insurance against influenza strain diversity", Expert Rev Vaccines, 10(4):447-462, (2011).
O Kistner et al., "Development of a mammalian cell (Vero) derived candidate influenza virus vaccine", Vaccine, 16(9-10):960-968, (1998).
Odagiri, T. (2012) "Methods to select influenza vaccine strain and problems in vaccine, future perspective for improvement" *Shoni-Ka (Paediatric Service)*, 53(10):1355-1365.
Office Action dated Aug. 16, 2012, for U.S. Appl. No. 12/448,057, filed Dec. 5, 2007, 13 pages.
Office Action dated Jan. 2, 2015, for U.S. Appl. No. 12/448,057, filed Dec. 5, 2007, 12 pages.
Office Action, dated Dec. 18, 2014, for U.S. Appl. No. 14/035,668, filed Sep. 24, 2013, 14 pages.
Ott et al., "Enhancement of humoral response against human influenza vaccine with the simple submicron oil/water emulsion adjuvant MF59," Vaccine, 13(16):1557-1562, (1995).
Ott et al., "MF59. Design and evaluation of a safe and potent adjuvant for human vaccines," Pharm Biotechnol, 6:277-296, (1995).
Palache et al., "Immunogenicity and reactogenicity of influenza subunit vaccines produced in MDCK cells or fertilized chicken eggs", J Infec Dis, 176 Suppl 1:S20-23, (1997).
Palese (2006) "Making better influenza virus vaccines?" *Emerg Infect Dis*, 12(1):61-5.
Palker et al., "Protective efficacy of intranasal cold-adapted influenza A/New Caledonia/20/99 (H1N1) vaccines comprised of egg- or cell culture derived-reassortants", Virus Res, 105(2):183-194, (2004).
Park et al., "Biodegradable polymer microneedles: fabrication, mechanics and transdermal drug delivery", *Proceedings of the 26th Annual International Conference of the IEEE EMBS*, San Francisco, CA, pp. 2654-2657, (2004).
Pau et al., "The human cell line PER.C6 provides a new manufacturing system for the production of influenza vaccines", *Vaccine*, 19(17-19):2716-21, (2001).
Peltola et al., "Influenza A and B virus infections in children", *Clin Infect Dis*, 36(3):299-305, (2003).
Petrovsky et al., "Vaccine adjuvants: current state and future trends", Immunol Cell Biol, 82(5):488-496, (2004).
Petrovsky et al., "New-Age Vaccine Adjuvants: Friend or Foe? A major unsolved challenge in adjuvant development is how to achieve a potent adjuvant effect while avoiding reactogenicity or toxicity", downloaded Dec. 18, 2011 from Biopharminternational.com.
Piascik, "Intranasal flu vaccine available this season", *J Am Pharm Assoc*, 43(6):728-30, (2003).

(56) References Cited

OTHER PUBLICATIONS

Pickering et al., "Influenza virus pyrogenicity: central role of structural orientation of virion components and involvement of viral lipid and glycoproteins", J Gen Virol, 73(Pt 6):1345-1354, (1992).
Pien (2004). "Statement Presented to Committee on Aging United States Senate," Retrieved Dec. 4, 2014 from <http://www.aging.senate.gov/imo/media/doc/hr133hp.pdb>.
Plotkin and Orenstein. Vaccines, 4th Edition, Sep. 19, 2003, p. 349.
Plotnicky et al., "The immunodominant influenza matrix T cell epitope recognized in human induces influenza protection in HLA-A2/K(b) transgenic mice", Virology, 309(2):320-329, (2003).
Podda (2001) "The adjuvanted influenza vaccines with novel adjuvants: experience with the MF59-adjuvanted vaccine" Vaccine, 19(17-19):2673-80.
Podda (2003) "MF59-adjuvanted vaccines: increased immunogenicity with an optimal safety profile" Expert Rev Vaccines, 2(2):197-203.
Poehling et al., "The underrecognized burden of influenza in young children", N Engl J Med, 355(1):31-40, (2006).
Powell & Newman, eds., Vaccine Design: The Subunit and Adjuvant Approach, Plenum Press, ISBN 0-306-44867-X, (1995).
Prausnitz, "Microneedles for transdermal drug delivery", Adv Drug Deliv Rev, 56(5):581-7, (2004).
Principi et al., Pediatr Infect Dis J, 22(10 Suppl):S207-10, (2003).
Reina et al. (1997) "Comparison of Madin-Darby canine kidney cells (MDCK) with a green monkey continuous cell line (Vero) and human lung embryonated cells (MRC-5) in the isolation of influenza A virus from nasopharyngeal aspirates by shell vial culture" J Clin Microbiol, 35(7):1900-1.
Remarque et al. (1998) "Altered Antibody Response to Influenza H1N1 Vaccine in Healthy Elderly People as Determined by HI, ELISA and Neutralization Assay" J Med Viro, 55:82-87.
Response to Office Action, dated Feb. 15, 2013, for U.S. Appl. No. 12/448,057, filed Dec. 5, 2007, 14 pages.
Response to Office Action, dated Aug. 27, 2013, for U.S. Appl. No. 12/448,057, filed Dec. 5, 2007, 16 pages.
Response to Final Office Action, dated Apr. 3, 2014, for U.S. Appl. No. 12/448,057, filed Dec. 5, 2007, 18 pages.
Response to Office Action dated Apr. 2, 2015, for U.S. Appl. No. 12/448,057, filed Dec. 5, 2007, 10 pages.
Response to Final Office Action and Advisory Action, dated Jul. 2, 2014, for U.S. Appl. No. 12/448,057, filed Dec. 5, 2007, 14 pages.
Response to Office Action, dated Mar. 18, 2015, for U.S. Appl. No. 14/035,668, filed Sep. 24, 2013, 13 pages.
Response to Notice of Opposition, filed in opposition against EP2121011, dated Oct. 6, 2015, 10 pages.
Robertson et al. (1990) "The hemagglutinin of influenza B virus present in clinical material is a single species identical to that of mammalian cell-grown virus" Virology, 179(1):35-40.
Rocha et al. (1993) "Comparison of 10 influenza A (H1N1 and H3N2) haemagglutinin sequences obtained directly from clinical specimens to those of MDCK cell- and egg-grown viruses" J Gen Virol, 74(Pt 11):2513-8.
Rota et al. (1990) "Cocirculation of two distinct evolutionary lineages of influenza type B virus since 1983" Virology, 175(1):59-68.
Rota et al. (1992) "Antigenic and genetic characterization of the haemagglutinins of recent cocirculating strains of influenza B virus" J Gen Virol, 73(Pt 10):2737-42.
Saito et al. (2004) "Antigenic alteration of influenza B virus associated with loss of a glycosylation site due to host-cell adaptation" Journal of Medical Virology, 74:336-343.
Sakoh, M. (Nov. 1989) "Antibody response of influenza vaccine and laboratory examination of prevaccination in the aged" Kurume-Igakukaizassi (Journal of KURUME Association of Medical Science), 52(11):1157-1167.
Scheifele et al., "Ocular and respiratory symptoms attributable to inactivated split influenza vaccine: evidence from a controlled trial involving adults", Clin Infect Dis, 36(7):850-857, (2003).

Schild et al., "Single-radial haemolysis: a new method for the assay of antibody to influenza haemagglutinin", Bull World Health Organ, 52(1):43-50, (1975).
Schneider et al. (Apr. 1, 1996) "Antibody response to tetravalent influenza subunit vaccine in patients infected with human immunodeficiency virus type 1" Int J Antimicrob Agents, 6(4):195-200.
Schuind et al., "Immunogenicity and Safety of an EB66 Cell-Culture-Derived Influenza A/Indonesia/5/2005 (H5N1) AS03-Adjuvanted Vaccine: A Phase 1 Randomized Trial", J Infect Dis, 212(4):531-541, (2015).
Schultze et al. (2008) "Safety of MF59(TM) adjuvant" Vaccine, vol. 26 (2008), pp. 3209-3222.
Sigma Catalogue Excerpt: Squalene, (1998).
Sigma Catalogue Excerpt: α-Tocopherol, (1998).
Sigma-Aldrich "Product Information: Tween 80 Sigma Ultra, Product No. P 8074," product information pamphlet, 2 pages, (2006).
Singh el al., "A novel bioadhesive intranasal delivery system for inactivated influenza vaccines," J Control Release, 70(3):267-276, (2001).
Singh et al., "Cationic microparticles are an effective delivery system for immune stimulatory cpG DNA," Pharm Res, 18(10):1476-1479, (2001).
Singh et al., "A preliminary evaluation of alternative adjuvants to alum using a range of established and new generation vaccine antigens", Vaccine, 24(10):1680-1686, (2006).
Skowronski et al., "Does antigen-specific cytokine response correlate with the experience of oculorespiratory syndrome after influenza vaccine?," J Infect Dis, 187(3):495-499, (2003).
Skowronski et al., "Estimating vaccine effectiveness against laboratory-confirmed influenza using a sentinel physician network: results from the 2005-2006 season of dual A and B vaccine mismatch in Canada", Vaccine, 25(15):2842-51, (2007).
Squarcione et al., "Comparison of the reactogenicity and immunogenicity of a split and a subunit-adjuvanted influenza vaccine in elderly subjects", Vaccine, 21(11-12):1268-1274, (2003).
Stephenson et al., "Boosting immunity to influenza H5N1 with MF59-adjuvanted H5N3 A/Duck/Singapore/97 vaccine in a primed human population," Vaccine, 21(15):1687-1693, (2003).
Stills, "Adjuvants and antibody production: dispelling the myths associated with Freund's complete and other adjuvants," ILAR J, 46(3):280-293, (2005).
Sugimura et al., "Improved antibody responses in infants less than 1 year old using intradermal influenza vaccination", Vaccine, 26(22):2700-5, (2008).
Tada, Y. (Jan. 2010) "Novel A(H1N1) Inactivated Influenza Split Vaccine" Rinsho-to-uirusu (Clinical and Virus), 38(1):62-75.
Tada, Y. (Oct. 2010) "Influenza Vaccine" Rinsho-to-biseibutsu (Clinical and Microorganism), 37:053-060.
Tetsuo Nakayama, Kaisetsu "Tokushuu Influenza Influenza vaccine no kaihatsu to kyoukyuu" ("Special topics Influenza; Development and Supply of Influenza Vaccine"), Sougou Rinsho (General Clinic), Feb. 1, 2000, vol. 49, No. 2, p. 238-244.
Third party observations to European Patent Application No. 07866632.8 (EP2121011), dated Oct. 7, 2013.
Toews et al., "Mass spectrometric identification of formaldehyde-induced peptide modifications under in vivo protein cross-linking conditions", Anal Chim Acta, 618(2):168-183, (2008).
Transcript pp. 1 to 100 (Feb. 28, 2007) "Influenza B Strain—Discussion of Circulating Lineages Introduction" Vaccines and Related Biological Products Advisory Committee, FDA, 100 pages.
Transcript pp. 201 to 308 (Feb. 28, 2007) "Influenza B Strain—Discussion of Circulating Lineages Introduction" Vaccines and Related Biological Products Advisory Committee, FDA, 108 pages.
Treanor et al., "Evaluation of a recombinant hemagglutinin expressed in insect cells as an influenza vaccine in young and elderly adults", J Infect Dis, 173(6):1467-70, (1996).
Tsai et al. (2006) "Increasing appearance of reassortant influenza B virus in Taiwan from 2002 to 2005" J Clin Microbiol, 44(8):2705-13.
Ulmer et al., "Vaccine manufacturing: challenges and solutions," Nat Biotechnol, 24(11):1377-1383, (2006).

(56) References Cited

OTHER PUBLICATIONS

Valensi et al., "Systemic cytokine profiles in BALB/c mice immunized with trivalent influenza vaccine containing MF59 oil emulsion and other advanced adjuvants," J Immunol 153(9):4029-4039, (1994).
Vanlandschoot et al., "Recombinant secreted haemagglutinin protects mice against a lethal challenge of influenza virus," Vaccine, 11(12):1185-1187, (1993).
Vasilakos et al., "Adjuvant activities of immune response modifier R-848: comparison with CpG ODN," Cell Immunol, 204(1):64-74, (2000).
Vermout et al., "Choix d'un adjuvant lors d'essais de vaccination," Ann Méd Vét, 147:393-401, (2003).
Vesikari et al. (2009) "Enhanced Immunogenicity of Seasonal Influenza Vaccines in Young Children Using MF59 Adjuvant" *The Pediatric Infectious Disease Journal*, 28(7):563-571.
Vesikari et al., "Oil-in-water emulsion adjuvant with influenza vaccine in young children", N Engl J Med, 365(15):1406-16, (2011).
VRBPAC Teleconference Mar. 6, 2002 Preliminary Summary, 1 page.
Wack et al., "Combination adjuvants for the induction of potent, long-lasting antibody and T-cell responses to influenza vaccine in mice", Vaccine, 26(4):552-561, (2008).
Walter et al., *Pediatrics*, 118(3):e570-78, (2006).
Weeke-Lüttmann et al., "Anti-ovalbumin sensitizing ability in influenza vaccines in guinea pigs", Dev Biol Stand, 39:219-222, (1977).
Weeratna et al., "CpG DNA induces stronger immune responses with less toxicity than other adjuvants," Vaccine, 18(17):1755-1762, (2000).
Weeratna et al., "TLR agonists as vaccine adjuvants: comparison of CpG ODN and Resiquimod (R-848)," Vaccine, 23(45):5263-5270, (2005).
Weir (Feb. 28, 2007) "Influenza B Strain—Discussion of Circulating Lineages Introduction" Vaccines and Related Biological Products Advisory Committee, FDA, 75 pages.
Weller et al., "Split virus influenza vaccination in children: an evaluation of efficacy", Curr Med Res Opin, 9(10):713-715, (1985).
WHO (1991) "Recommended composition of influenza virus vaccines for use in the 1991-1992 season" 66(9):57-64.
WHO (Feb. 14, 2006) "Recommended composition of influenza virus vaccines for use in the 2006-2007 influenza season" 5 pages.
WHO (Feb. 2012) "Recommended composition of influenza virus vaccines for use in the 2012-2013 northern hemisphere influenza season" 16 pages.
WHO (Feb. 2013) "Recommended composition of influenza virus vaccines for use in the 2013-2014 northern hemisphere influenza season" 21 pages.
WHO (Feb. 2014) "Recommended composition of influenza virus vaccines for use in the 2014-2015 northern hemisphere influenza season" 15 pages.
WHO Questions and Answers (Feb. 2014) "Recommended composition of influenza virus vaccines for use in the northern hemisphere 2014-15 influenza season and development of candidate vaccine viruses for pandemic preparedness" 4 pages.
WHO (Sep. 2013) "Recommended composition of influenza virus vaccines for use in the 2014 southern hemisphere influenza season" 17 pages.
William Egan, Testimony published by FDA United States of Department of Health & Human Services, Oct. 5, 2004.
Wollenberg et al., "Plasmacytoid dendritic cells: a new cutaneous dendritic cell subset with distinct role in inflammatory skin diseases", J Invest Dermatol, 119(5):1096-102, (2002).
De Wit et al., "Protection of mice against lethal infection with highly pathogenic H7N7 influenza A virus by using a recombinant low-pathogenicity vaccine strain", J Virol, 79(19):12401-12407, (2005).
Wood et al., "Experience with the clinical development of influenza vaccines for potential pandemics", Med Microbiol Immunol, 191(3-4):197-201, (2002).
Woodhour et al., "Development and Application of New Parenteral Adjuvants. V. Comparative Potencies of Influenza Vaccines Emulsified in Various Oils," J Immunol, 86(6):681-689, (1961).
World Health Organization, "Recommendations for production and control of influenza vaccine (inactivated)", 33 pages, (2003).
Wong et al. (2005) "Influenza vaccination: options and issues" *Hong Kong Med J*, 11(5):381-90.
Wood (2002) "Selection of influenza vaccine strains and developing pandemic vaccines" *Vaccine*, 20 Suppl 5:B40-4.
Yasuda et al., "Comparison of half and full doses of an MF59-adjuvanted cell culture-derived A/H1N1v vaccine in Japanese children," Adv Ther 27(7):444-457, (2010).
Xu et al. (2001) "Multiple lineages co-circulation and genetic reassortment of the neuraminidase and hemagglutinin genes within influenza viruses of the same type/subtype," *International Congress Series*, 1219:383-387.
FLUAD® Product Monograph, No. ATC: J07BB02, Novartis Vaccines and Diagnostics, Inc., Cambridge, MA, May 8, 2013, pp. 1-27.

* cited by examiner

INFLUENZA VACCINES WITH REDUCED AMOUNTS OF SQUALENE

CROSS REFERENCE TO RELATED APPLICATIONS

This application is a continuation of U.S. application Ser. No. 16/178,897, filed Nov. 2, 2018, now abandoned, which is a continuation of U.S. application Ser. No. 15/007,719, filed Jan. 27, 2016, now U.S. Pat. No. 10,149,901, which is a Continuation of U.S. patent application Ser. No. 13/148,939, filed Dec. 15, 2011, now U.S. Pat. No. 9,278,126, claiming an international filing date of Feb. 10, 2010; which is the National Stage of International Patent Application No. PCT/IB2010/000312, filed Feb. 10, 2010; which claims priority to U.S. Provisional Patent Application No. 61/207,385 filed Feb. 10, 2009; the disclosures of which are herein incorporated by reference in their entirety.

TECHNICAL FIELD

This invention is in the field of vaccines for protecting against influenza virus infection, and in particular vaccines that include reduced amounts of squalene relative to marketed vaccines.

BACKGROUND ART

Influenza vaccines generally do not include an adjuvant, except for the PREPANDRIX™ product (GlaxoSmithKline) and the FLUAD™ product (Novartis Vaccines). The adjuvant in the monovalent pre-pandemic seasonal PREPANDRIX™ vaccine is an oil-in-water emulsion. The antigen and the emulsion adjuvant are supplied in separate 10-dose vials for mixing at the point of use at a 1:1 volume ratio. The product datasheet shows that each dose has a volume of 0.5 mL and contains 3.75 µg HA with 10.68 mg squalene and 4.85 mg polysorbate 80.

The adjuvant in the trivalent seasonal FLUAD™ vaccine is an oil-in-water emulsion. The antigen and the emulsion adjuvant are supplied in pre-mixed format in a pre-filled syringe. The product datasheet shows that each dose has a volume of 0.5 mL and contains 15 µg hemagglutinin (HA) per strain with 9.75 mg squalene and 1.175 mg polysorbate 80. As disclosed in reference 1, the vaccine is made by mixing at a 2× emulsion with a 2× antigen solution at a 1:1 volumetric ratio, to give a final solution with both emulsion and antigen at the 1× concentration. This 1:1 mixing ratio is further explained in chapter 10 of reference 75. Modifications of this mixing are disclosed in reference 2.

Compared to the FLUAD™ product, reference 3 discloses trivalent influenza vaccines with lower amounts of HA (3×5 µg HA/dose) and lower amounts of squalene (5.35 mg/dose). The vaccine includes thiomersal preservative and was administered to humans as a 0.5 mL dose.

It is an object of the invention to provide further and improved formulations of adjuvanted influenza vaccines, and in particular of seasonal influenza vaccines.

DISCLOSURE OF THE INVENTION

In one embodiment, the invention provides an influenza virus vaccine comprising: (i) hemagglutinin from at least one influenza A virus strain and at least one influenza B virus strain, wherein the hemagglutinin concentration is >12 µg/ml per strain; and (ii) an oil-in-water emulsion adjuvant with submicron oil droplets, comprising squalene, where the squalene concentration is <19 mg/ml.

In another embodiment, the invention provides a mercury-free influenza virus vaccine comprising: (i) hemagglutinin from at least one influenza A virus strain and at least one influenza B virus strain; and (ii) an oil-in-water emulsion adjuvant with submicron oil droplets, comprising squalene, where the squalene concentration is <19 mg/ml.

In another embodiment, the invention provides on influenza virus vaccine having a unit dose volume between 0.2-0.3 mL, wherein the vaccine comprises: (i) hemagglutinin front at least one influenza A virus strain and at least one influenza B virus strain; and (ii) an oil-in-water emulsion adjuvant with submicron oil droplets, comprising squalene, where the squalene concentration is ≤19 mg/ml.

In another embodiment, the invention provides an influenza virus vaccine comprising: (i) hemagglutinin from at least one influenza A virus strain and at least one influenza B virus strain; and (ii) an oil-in-water emulsion adjuvant with submicron oil droplets, comprising squalene, where the squalene concentration is 9.75 mg/mL or 4.88 mg/mL.

In another embodiment, the invention provides an influenza virus vaccine having a unit dose volume between 0.2-0.3 mL, comprising: (i) hemagglutinin from at least one influenza A virus strain and at least one influenza B virus strain; and (ii) an oil-in-water emulsion adjuvant with submicron oil droplets, comprising squalene, where the squalene concentration is 19.5 mg/mL, 9.75 mg/mL or 4.88 mg/mL.

In another embodiment, the invention provider an influenza virus vaccine comprising: (i) hemagglutinin from at least two influenza A virus strains and at least two Influenza B virus strains; and (ii) an oil-in-water emulsion adjuvant with submicron oil droplets, comprising squalene, where the squalene concentration is ≤mg/mL.

Vaccine Preparation

Various forms of influenza virus vaccine are currently available, and vaccines are generally based either on live virus or on inactivated virus. Inactivated vaccines may be based on whole virions, split virions, or on purified surface antigens. Influenza antigens can also be presented in the form of virosomes. The invention can be used with any of these types of vaccine, but will typically be used with inactivated vaccines.

Where an inactivated virus is used, the vaccine may comprise whole virion, split virion, or purified surface antigens (including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfuilerene (C60), binary ethylamine, acetyl ethyleneimine, or combinations thereof. Non-Chemical methods of viral inactivation are known in the art, such as for example UV light or gamma irradiation.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 4-9, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecarneg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene ester, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The PREPANDRIX™, BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, FLUAD™, AGRIPPAL™ and INFLUVAC™ products are examples.

Another form of inactivated influenza antigen is the virosome [10] (nucleic acid free viral-like liposomal particles), as in the INFLEXAL V™ and INVAVAC™ products. Virosomes can be prepared by solubilization of influenza virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with vital proteins in their membrane.

Strain Selection

Vaccines of the invention include hemagglutinin from at least one influenza A virus strain and at least one influenza B virus strain. The different strains will typically be grown separately and then mixed after the viruses have been harvested and antigens have been prepared. Thus a process of the invention may include the step of mixing antigens from more than one influenza strain.

Strains used with the invention may have a natural HA as found in a wild-type virus, or a modified HA. For instance, it is known to modify HA to remove determinants (e.g. hyper-basic regions around the HA1/HA2 cleavage site) that cause a vims to be highly pathogenic in avian species. Hemagglutinins of influenza B viruses used with the invention preferably have Asn at amino acid 197, providing a glycosylation site [11].

An influenza virus used with the invention may be a reassortant strain, and may have been obtained by reverse genetics techniques. Reverse genetics techniques [e.g. 12-16] allow influenza viruses with desired genome segments to be prepared in vitro using plasmids or other artificial vectors. Typically, it involves expressing (a) DMA molecules that encode desired viral RNA molecules e.g. from poll promoters or bacteriophage RNA polymerase promoters, and (b) DNA molecules that encode viral proteins e.g. from poll promoters, such that expression of both types of DMA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA con be used [17-19], and these methods will also involve the use of plasmids to express all or some (e.g. just the PB1, PB2, PA and NP proteins) of the viral proteins, with up to 12 plasmids being used in some methods. To reduce the number of plasmids needed, one approach [20] combines a plurality of RNA polymerase 1 transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 20 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using poll promoters to encode the viral RNA segments, it is possible to use bacteriophage polymerase promoters [21]. For instance, promoters for the SP6, T3 of T7 polymerases can conveniently be used. Because of the species-specificity of poll promoters, bacteriophage polymerase promoters can be more convenient for many cell types (e.g. MDCK), although a cell must also be transfected with a plasmid encoding the exogenous polymerase enzyme.

In other techniques it is possible to use dual poll and polII promoters to simultaneously code for the viral RNas and for expressible mRNAs from a single template [22,23].

Thus an influenza A virus may include one or more RNA segments from a A/PR/8/34 virus (typically 6 segments from A/PR/8/34, with the HA and N segments being from a vaccine strain, i.e. a 6:2 reassortant). It may also include one or more RNA segments from a A/WSN/33 virus, or from any other virus strain useful for generating reassortant viruses for vaccine preparation. An influenza A virus may include fewer than 6 (i.e. 0, 1, 2, 3, 4 or 5) viral segments from an AA/6/60 influenza virus (A/Ann Arbor/6-60). An influenza B vires may include fewer than 6 (i.e. 0, 1, 2, 3, 4 or 5) viral segments from an AA/1/66 influenza virus (B/Ann Arbor/1/66). Typically, the invention protects against a strain that is capable of human-to-human transmission, and so the strain's genome will usually include it least one RNA segment that originated in a mammalian (e.g. in a human) influenza virus. It may include NS segment that originated in an avian influenza virus.

Strains whose antigens can be included in the compositions may be resistant to antiviral therapy (e.g. resistant to oseltamivir [24] and/or z-zanamivir), including resistant pandemic strains [25].

Particularly useful strains are those that have not been passaged through eggs at any stage between isolation from a patient and replication in a cell culture system, inclusive. MDCK cells can be used exclusively of for all steps front isolation to virus replication.

In some embodiments, strains used with the invention have hemagglutinin with a binding preference for oligosaccharides with a Sia(α2,6)Gal terminal disaccharide compared to oligosaccharides with a Sia(α2,3)Gal terminal disaccharide. Human influenza viruses bind to receptor oligosaccharides having a Sia(α2,6)Gal terminal disaccharide (sialic acid linked α-2,6 to galactose), but eggs and Vero cells have receptor oligosaccharides with a Sia(α2,3)Gal terminal disaccharide. Growth of human influenza viruses in cells such as MDCK provides selection pressure on hemagglutinin to maintain the native Sia(α2,6)Gal binding, unlike egg passaging.

To determine if a virus has a binding preference for oligosaccharides with a Sia(α2,6)Gal terminal disaccharide compared to oligosaccharides with a Sia(α2,3)Gal terminal disaccharide, various assays can be used. For instance, reference 26 describes a solid-phase enzyme-linked assay for influenza virus receptor-binding activity which gives sensitive and quantitative measurements of affinity constants. Reference 27 used a solid-phase assay in which binding of viruses to two different sialylglycoproteins was assessed (ovomucoid, with Sia(α2,3)Gal determinants; and pig α$_2$-macroglobulin, which Sia(α2,6)Gal determinants), and also describes an assay in which the binding of virus was assessed against two receptor analogs: free sialic acid (Neu5Ac) and 3'-sialyllactose (Neu5Acα2-3Galβ1-4Glc). Reference 28 reports an assay using a glycan array which was able to clearly differentiate receptor preferences for α2,3 or α2,6 linkages. Reference 29 reports an assay based on agglutination of human erythrocytes enzymatically modified to contain either Sia(α2,6)Gal or Sia(α2,3)Gal. Depending on the type of assay, it may be performed directly with the virus itself, or can be performed indirectly with hemagglutinin purified from the virus.

In some embodiments influenza strains used with the invention have glycoproteins (including hemagglutinin) with a different glycosylation patient from egg-derived viruses. Thus the glycoproteins will include glycoforms that are nor seen in chicken eggs.

Influenza A virus currently displays sixteen HA subtypes: H1, H2, H3, H4, H5, H6, H7, H8, H9, H10, H11, H12, H13, H14, H15 and H16. The invention may protect against one or more of these subtypes. The invention may protect against one or more of influenza A virus NA subtypes N1, N2, N3, N4, N5, N6, N7, N8 or N9. Vaccines herein include antigen from it least one influenza A virus strain, and will typically include antigen from at least two influenza A virus strains e.g. 2 or 3 influenza A virus strains. Where two influenza A virus strains are included, these will usually be a H1 strain and a H3 strain. Where three influenza A virus strains are included, these will usually be a H1 strain, a H3 strain and a pandemic-associated strain. In some embodiments the H3 strain cross-reacts with A/Moscow/10/99; in other embodiments the H3 strain cross-reacts with A/Fujian/411/2092.Ref.30 discloses vaccines including A/H1N1, A/H3N2, A/H5N1 and B antigens.

Characteristics of a pandemic-associated influenza strain are; (a) it contains a new hemagglutinin compared to the hemagglutinins in currently-circulating human strains, i.e. one that has not been evident in the human population for over a decade (e.g. H2), or has not previously been seen at all in the human population (e.g. H5, H5 or H9, that have generally been found only in bird populations), such that the vaccine recipient and the general human population are immunologically naïve to the strain's hemagglutinin; (b) It is capable of being transmitted horizontally in the human population; and (c) it is pathogenic to humans. A pandemic-associated influenza virus strain for use with the invention will typically have a H2, H5, H7 or H9 subtype e.g. H5N1, H5N3, H9N2, H2N2, H7N1 or H7N7, H5N1 strains are preferred. Pandemic strains can have a H1 subtype (e.g. H1N1); for example, the HA can be immunologically cross-reactive with the A/California/04/09 strain.

Influenza B virus currently does not display different HA subtypes, but influenza B virus strains do fall into two distinct lineages. These lineages emerged in the late 1980's and have HAs which can be antigenically and/or genetically distinguished from each other [31]. Current influenza B virus strains are either B/Victoria/2/87-like or B/Yamagata/16/88-like. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [32].

In some embodiments, compositions of the invention include antigen from a single influenza B virus strain, and this strain may be B/Victoria/2/87-like or B/Yamagata/16/88-like. In other embodiments, however, compositions of the invention include antigen from two influenza B virus strains, and these will typically include a B/Victoria/2/87-like strain and a B/Yamagata/16/88-like strain.

Preferred vaccines of the invention include antigen from two influenza A virus strains and two influenza B virus strains ("ABBA" vaccines). Thus preferred ABBA vaccines of the invention will include hemagglutinin from: (i) a H1N1 strain; (ii) a H3N2 strain; (iii) a B/Victoria/2/87-like strain; and (iv) B/Yamagata/16/88-like strain.

In some ABBA embodiments, at least two of the influenza B virus strains may have distinct hemagglutinins but related neuraminidases. For instance, they may both have a B/Victoria/2/87-like neuraminidase [33] or may both have a B/Yamagata/16/88-like neuraminidase. For instance, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline; at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not t praline at residue 88, but preferably a glutamine. Similarly, in some embodiments the neuraminidase may have a deletion at residue 43, or it may have a threonine; a deletion at residue 43, arising from a trinucleotide deletion in the NA gene, has been reported as a characteristic of B/Victoria/2/87-like strains, although recent strains have regained Thr-43 [33]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [34]. Thus an ABBA vaccine may use two B strains that are antigenically distinct for HA (one B/Yamagata/16/88-like, one B/Victoria/2/87-like), but are related for NA (both B/Yamagata/16/88-like, or both B/Victoria/2/87-like).

The invention is not restricted to 3-valent and 4-valent vaccines, but encompasses 5-valent, 6-valent, 7-valent, etc. vaccines. An example 5-valent vaccine may include three influenza A strains (e.g. one H1 strain and two H3 strains, as discussed above) plus two influenza B strains. For example, an A-A-A-B-B vaccine may include hemagglutinin front: (i) a H1N1 strain; (ii) a A/Moscow/10/99-like H3N2 strain; (iii) a A/Fujian/411/2002-like H3N2 strain; (iv) a B/Victoria/2/87-like strain; and (v) a B/Yamagata/16/88-like strain. Another A-A-A-B-B vaccine may include hemagglutinin from: (i) a H1N1 strain; (ii) a H3N2 strain; (iii) a H5 influenza A virus strain, such as a H5N1 strain; (iv) a B/Victoria/2/87-like strain; and (v) a B/Yamagata/16/88-like strain. An A-A-A-A-B vaccine may include hemagglutinin from: (i) a H1N1 strain; (ii) a A/Moscow/10/99-like H3N2 strain; (iii) a A/Fujian/411/2002-like H3N2 strain, (iv) a H5 influenza A virus strain, such as a H5N1 strain; and (v) an influenza B virus strain. An A-A-A-A-B-B vaccine may include hemagglutinin from: (i) a H1N1 strain; (ii) a A/Moscow/10/99-like H3N2 strain; (iii) a A/Fujian/411/2002-like H3N2 strain; (iv) a H5 influenza A virus strain, such as a H5N1 strain; (v) a B/Victoria/2/87-like strain; and (vi) a B/Yamagata/16/88-like strain.

Hemagglutinin Dosing

Hemagglutinin (HA) is the main immunogen in current inactivated influenza vaccines, and vaccine doses are standardised by reference to HA levels, typically measured by SRID. Existing vaccines typically contain about 15 μg of HA per strain in a 0.5 ml dose, although lower doses can be used e.g. for children (typically a 0.25 mkL dose at the same HA concentration), or in pandemic situations, or when using an adjuvant. Fractional doses such as ½ (i.e. 7.5 μg HA per strain), ¼ and ⅛ have been used, as have higher doses (e.g. 3× or 9× doses [35,36]).

In general, the amount of HA per dose can be in the range 0.1 and 150 μg per strain, preferably between 0.1 and 50 μg e.g. 0.1-20 μg, 0.1-1.5 μg, 0.1-10 μg, 0.1-7.5 μg, 0.5-5 μg, etc. Particular doses include e.g. about 45, about 30, about 15, about 10, about 7.5, about 5, about 3-8, about 1-9, about 1.5, etc. μg per strain. In some embodiments of the invention, the concentration of HA per strain in a composition is at least 12 μg/ml (i.e. at least 6 μg per strain in a 0.5 mL volume, which is higher than the concentration used in reference 3). Usually the concentration will be ≥15 μg/ml e.g. ≥20 μg/ml, ≥25 μg/ml, ≥30 μg/ml or more. A concentration of 15 μg/ml per strain or 30 μg/ml per strain is typical.

Normally the concentration of HA will be the same for each strain in a composition. In some embodiments, however, the concentrations will all be integer multiples of the lowest concentration. For example, if the lowest HA concentration for a particular strain is 15 μg/ml then the other HA concentrations in the composition will be 15 μg/ml, 20 μg/ml, 45 μg/ml or 60 μg/ml.

As mentioned above, the invention will usually be used with inactivated vaccines. In some embodiments, however, it can be used with live vaccines. Rather than being standardized around HA content, live vaccines dosing is measured by median tissue culture infectious dose ($TCID_{50}$). A $TCID_{50}$ of between $10^6$ and $10^8$ (preferably between $10^{6.5}$-$10^{7.5}$) per strain is typical. The influenza virus may be attenuated. The influenza virus may be temperature-sensitive. The influenza virus may be cold-adapted.

Cell Lines

Manufacture of vaccines for use with the invention can use SPF eggs as the substrate for viral growth, wherein virus is harvested from infected allantoic fluids of hens' eggs. Instead, however, cell lines which support influenza virus replication may be used. The cell line will typically be of mammalian origin. Suitable mammalian cells of origin include, but are not limited to, hamster, cattle, primate (including humans and monkeys) and dog cells, although the use of primate cells is not preferred. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line (37-39). Suitable dog cells are e.g. kidney cells, as in the CLDK and MDCK cell lines.

Thus suitable cell lines include, but are not limited to: MDCK; CHO; CLDK; HKCC; 293T; BHK; Vero; MRC-5; PER.C6 [40]; FRhL2; WI-38; etc. Suitable cell lines are widely available e.g. from the American Type Cell Culture (ATCC) collection [41], from the Coriell Cell Repositories [42], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The most preferred cell lines are those with mammalian-type glycosylation. As a less-preferred alternative to mammalian cell lines, virus can be grown on avian cell lines [e.g. refs. 43-45], including cell lines derived from ducks (e.g. duck retina) or hens. Examples of avian cell lines include avian embryonic stem cells [43,46] and duck retina cells [44]. Suitable avian embryonic stem cells, include the EBx cell line derived from chicken embryonic stem cells, EB45, EB14, and EB14-074 [47]. Chicken embryo fibroblasts (CEF) may also be used. Rather than using avian cells, however, the use of mammalian cells means that vaccines can be free from avian DNA and egg proteins (such as ovalbumin and ovomucoid), thereby reducing allergenicity.

The most preferred cell lines for growing influenza viruses are MDCK cell lines [48-51], derived from Madin Darby canine kidney. The original MDCK cell line is available from the ATCC as CCL-34, but derivatives of this cell line and other MDCK cell lines may also be used. For instance, reference 48 discloses a MDCK cell line that was adapted for growth in suspension culture ('MDCK 33016', deposited as DSM ACC 2219). Similarly, reference 52 discloses a MDCK-derived cell line that grows in suspension in serum-free culture ('B-702', deposited as PERM BP-7449). Reference 53 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 54 discloses MDCK cell lines with high susceptibility to infection, including 'MDCK.5P1' cells (ATCC CRL-12042). Any of these MDCK cell lines can be used.

Virus may be grown on cells in adherent culture or in suspension. Microcarrier cultures can also be used. In some embodiments, the cells may thus be adapted for growth in suspension.

Cell lines are preferably grown in serum-free culture media and/or protein free media. A medium is referred to as a serum-free medium in the context of the present invention in which there are no additives from scrum of human or animal origin. The cells growing in such cultures naturally contain proteins themselves, but a protein-free medium is understood to mean one in which multiplication of the cells (e.g. prior to infection) occurs with exclusion of proteins, growth factors, other protein additives and non-scrum proteins, but can optionally include proteins such as trypsin or other proteases that may be necessary for viral growth.

Cell lines supporting influenza virus replication are preferably grown below 37° C. [55] (e.g. 30-36° C., or at about 30° C., 31° C., 32° C., 33° C., 34° C., 35° C., 36° C.) during viral replication.

Methods for propagating influenza virus in cultured cells generally includes the steps of inoculating a culture of cells with an inoculum of the strain to be grown, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours pot infection. Still more preferably, the cells are harvested 38 to 40 hours post infection. Proteases (typically trypsin) are generally added during cell culture to allow viral release, and the proteases can be added at any suitable stage during the culture e.g. before inoculation, at the same time as inoculation, or after inoculation [55].

In some embodiments, particularly with MDCK cells, a cell line is not passaged from the master working cell bank, beyond 40 population-doubling levels.

The viral inoculum und the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [56]. Absence of herpes simplex viruses is particularly preferred.

Host Cell DNA

Where virus has been grown on a cell line then it is standard practice to minimize the amount of residual cell line DNA in the final vaccine, in order to minimize any oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

Vaccines containing <1 ng (e.g. <100 pg), host cell DNA per 15 µg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 µg of haemagglutinin are more preferred, as are vaccines containing <10 ng (e.g. <1 ng, <100 pg) host cell DNA per 0.5 ml volume.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 57 & 58, involving a two-step treatment, first using a DNase (e.g. Benzonase), which may be used during viral growth, and then a cationic detergent (e.g. CTAB), which may be used during virion disruption. Removal by β-propiolactone treatment can also be used.

Measurement of residual host cell DNA is now a routine regulatory requirement for biologicals and is within the normal capabilities of the skilled person. The assay used to measure DNA will typically be a validated assay [59,60]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three main techniques for DNA quantification can be used: hybridization methods, such as Southern blots or slot blots [61]; immunoassay methods, such as the Threshold™ System [62]; and quantitative PCR [63]. These methods are all familiar to the skilled person, although live precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used tor monitoring levels of contaminating DNA in biopharmaceuticals [62]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 64.

Pharmaceutical Compositions

Vaccines for use with the invention usually include components in addition to the influenza antigens e.g. they typically include one or more pharmaceutical carrier(s) and/or excipient(s). A thorough discussion of such components is available in reference 65. In many embodiments adjuvants may also be included.

Compositions will generally be in aqueous form at the point of administration.

A composition may include preservatives such as thiomersal or 2-phenoxyethanol. In some embodiments, however, the vaccine should, unlike the PREPANDRIX™ product, be substantially free from mercurial material e.g. thiomersal-free [8,66]. Vaccines containing no mercury are more preferred, and α-tocopherol succinate can be included as an alternative to mercurial compounds [8]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate, and/or magnesium chloride, etc. Where adjuvant is in a separate container from antigens, sodium chloride may be present in both containers.

Compositions may have an osmolality of between 200 mOsm/kg and 400 mOsm/kg, preferably between 240-360 mOsm/kg, maybe within the range of 290-310 mOsm/kg.

Compositions may include one or more buffers. Typical buffets include: a phosphate buffer; a Tris buffer, a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

Compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B). Where adjuvant is in a separate container from antigens, this detergent will usually be present in the antigen-containing container (e.g. antigen with polysorbate 80 and Octoxynol 10).

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human influenza vaccines are typically administered by intramuscular injection in a unit dosage volume of about 0.5 ml. In some embodiments of the invention, however, a unit dose with half this volume (i.e. about 0.2 ml) may be used. This reduced dosage volume is particularly useful with children. Even lower doses (e.g. 0.1 ml or 0.2 ml) may be useful e.g. for intradermal injection.

Vaccines are preferably stored at between 2° C. and 8° C. They should not be frozen. They should ideally be kept out of direct light.

Vaccines may be supplied in any suitable container, either formulated ready for administration or as a kit of parts for extemporaneous mixing prior to administration e.g. as separate antigen and adjuvant components (as in the PREPANDRIX™ product). Suitable containers include vials, syringes (e.g. disposable syringes), nasal sprays, etc. There containers should be sterile. Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass. A vial can have a cap (e.g. a Luer lock) adapted such that a syringe can be inserted into the cap. A vial may have a cap that permits aseptic removal of its contents, particularly for multidose vials. Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cup to seal the tip prior to attachment of a needle, and the lip cup is preferably made of a butyl rubber.

Containers may be marked to show a half-dose volume e.g. to facilitate delivery to children. For instance, a syringe containing a 0.5 ml dose may have a mark showing a 0.25 ml volume. Thus a vaccine may be packaged with a unit dose volume of 0.5 ml but may be administered as a unit dose volume of 0.25 ml, with this half dosing being facilitated by the container markings.

Where a glass container (e.g. a syringe or a vial) is used, then it is preferred to use a container made from a borosilicate glass rather than from a soda lime glass.

A container may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Adjuvants

At the point of use, vaccines of the invention may advantageously include an adjuvant, which can function to enhance the immune responses (humoral and/or cellular) elicited in a patient who receives the composition. The presence of an oil-in-water emulsion adjuvant (particularly one comprising squalene) has been shewn to enhance the strain cross-reactivity of immune responses for seasonal [67] and pandemic [68,69] influenza vaccines.

Oil-in-water emulsions for use with the invention typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil, etc. In the grain group, corn oil is the most readily available, but the oil of other cereal grains such as wheat, oats, rye, rice, teff, tricale, etc. may also be used. 6-10 carbon fatty acid esters of glycerol and 1,2-propanodiol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means accessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene. 2,6,10,15,19,23-hexamethyl-2,6,10,14,18,22-tetracosahexaene. Squalane, the saturated analog to squalene, can also be used. Fish oils, including squalene and squalane, are readily available from commercial sources or may be obtained by methods known in the art. Squalene is preferred.

Squalene-containing emulsions are already included in the FLUAD™ and PREPANDRIX™ products. In the FLUAD™ vaccine the total amount of HA is 45 µg (3×15 µg) and the total amount of squalane is 9.75 mg, in a dosage volume of 0.5 ml (i.e. 19.5 mg/ml squalene). In PREPANDRIX™ vaccine the total amount of HA is 3.75 µg (monovalent) and the total amount of squalene is 10.65 mg, also in a dosage volume of 0.5 ml (i.e. 21.4 mg/ml squalene). In many embodiments of the invention the squalene concentration is less than 19 mg/ml while still retaining an adjuvant effect, and the concentration may be ≤10 mg/ml e.g. ≤5 mg/ml, ≤2.5 mg/ml. A minimum amount of 0.5 mg squalene per dose is useful (e.g. see ref. 3). Examples of amounts per dose include 5.3 mg, 4.9 mg, 2.7 mg, 2.4 mg, 1.2 mg etc.

Other useful oils are the tocopherols, which are advantageously included in vaccines for use in elderly patients (e.g. aged 60 years or older) because vitamin E has been reported to have a positive effect on the immune response in this patient group [70]. They also have antioxidant properties that may help to stabilize the emulsion [71]. Various tocopherols exist (α, β, γ, δ, ε or ζ) but α is usually used. A preferred α-tocopherol is DL-α-tocopherol. α-tocopherol succinate is known to be compatible with influenza vaccines and to be a useful preservative as an alternative to mercurial compounds [8].

Mixtures of oils can be used e.g. squalene and α-tocopherol. An oil content in the range of 2-20% (by volume) is typical.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Nonionic surfactants are preferred. The most preferred surfactant for including in the emulsion is polysorbate 80 (polyoxyethylene sorbitan monooleate; Tween 80).

Mixtures of surfactants can be used e.g. Tween 80/Span 85 mixtures. A combination of a polyoxyethylene sorbitan ester and an octoxynol is also suitable. Another useful combination comprises laureth 9 plus a polyoxyethylene sorbitan ester and/or an octoxynol.

Preferred amounts of surfactant (% by weight) are; polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Squalene-containing oil-in-water emulsions are preferred, particularly those containing polysorbate 80. The weight ratio of squalene:polysorbate 80 may be between 1 and 10, for example between 2 and 9 e.g. about 2.2 or about 8.3. Specific-oil-in-water emulsion adjuvants useful with the invention include, but are not limited to:

- A submicron emulsion of squalene, polysorbate 80, and sorbitan trioleate. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [72-74], as described in more detail in Chapter 10 of ref. 75 and chapter 12 of ref. 76. The MF59 emulsion advantageously includes citrate ions e.g. 10 mM sodium citrate buffer.
- A submicron emulsion of squalene, a tocopherol, and polysorbate 80. These emulsions may have from 2 to 10% squalene, from 2 to 10% tocopherol and from 0.3 to 3% polysorbate 80, and the weight ratio of squalene:tocopherol is preferably ≤1 (e.g. 0.90) as this can provide a more stable emulsion. Squalene and polysorbate 80 may be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion has submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 01-4 mg polysorbate 80 [3].
- An emulsion of squalene, a tocopherol, and a Triton detergent (e.g. Triton X-100). The emulsion may also include a 3d-MPL (see below). This emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 µg/ml polysorbate 80, 110 µg/ml Triton X-100 and 100 µg/ml α-tocopherol succinate), and these concentrations should include any contribution of these components from antigens. The emulsion may also include squalene. The emulsion may also include a 3d-MPL. The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (77) (0.05-1% Thr/MDP, 5% squalane, 2.5% Pluronic L121 and 0.2% polysorbate 80). It can also be used without the Thr-MDP, as in the "Af" adjuvant [78] (5% squalane, 1.25% Pluronic L121 and 0.2% polysorbate 80). Microfluidisation is preferred.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 mm [79]. The emulsion may also include one or more of: alditol; a cryoprotective agent (e.g. a sugar, such as dodecylmaltoside and/or sucrose); and/or an alkylpolyglycoside. The emulsion may include a TLR4 agonist [80]. Such emulsions may be lyophilized.

An emulsion of squalene, poloxamer 105 and Abil-Care [81]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 82, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 83, produced by addition of aliphatic amine to desacylsaponin via the carboxyl group of glucuronic acid), dimethyldioctadecylammonium bromide and/or N,N-dioctadecyl-N, N-bis (2-hydroxyethyl)propanediamine.

An emulsion in which a saponin (e.g. QuilA or QS21) and a sterol (e.g. a cholesterol) are associated as helical micelles [84].

An emulsion comprising a mineral oil, a non-ionic lipophilic ethoxylated fatty alcohol, and a non-ionic hydrophilic surfactant (e.g. an ethoxylated fatly alcohol and/or polyoxyethylene-polyoxypropylene block copolymer) [85].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [85].

The emulsions may be combined with antigen(s) during vaccine manufacture, or may be supplied as a separate component for mixing with a separate antigen-containing component extemporaneously, at the time of delivery (as in the PREPANDRIX™ product). Where these two components are liquids then the volume ratio of the two liquids for mixing can vary (e.g. between 5:1 and 1:5) but is generally about 1:1.

After the antigen and adjuvant have been mixed, haemagglutinin antigen will generally remain in aqueous solution but may distribute itself around the oil/water interface. In general, little if any haemagglutinin will enter the oil phase of the emulsion.

The weight ratio of squalene to hemagglutinin (total amount) in a composition of the invention may be in the range from 20 to 180 e.g. 25-30, 50-60, 105-115.

Methods of Treatment, and Administration of the Vaccine

Compositions of the invention are suitable for administration to human patients, and the invention provides a method of raising an immune response in a patient, comprising the step of administering a composition of the invention to the patient.

The invention also provides a composition of the invention for use as a medicament.

The invention also provides the use of at least one influenza A virus antigen, at least one influenza B virus antigen, and squalene (e.g. in the form of an oil-in-water emulsion), in the manufacture of a composition for active immunization against influenza disease, wherein the composition is a vaccine having the characteristics described above.

These methods and uses will generally be used to generate an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [86]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg) but other available routes include subcutaneous injection, intradermal injection [87,88], intranasal [89-91], oral [92], buccal, sublingual, transcutaneous, transdermal [93], etc.

Vaccines prepared according to the invention may be used to treat both children and adults, influenza vaccines are currently recommended for use in pediatric and adult immunisation, from the age of 6 months. Thus the patient may be less then 1 year old, 6-<36 months old, 1-5 years old, 5-1.5 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, immunodeficient patients, patients who have taken an antiviral compound (e.g. on oseltarnivir or zanamivir compound; see below) in the 7 days prior to receiving the vaccine, people with egg allergies and people travelling abroad. The vaccines are not suitable solely for these groups, however, and may be used more generally in a population.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (<60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosel boost, a mucosal prime and parenteral boost, etc. Administration of more than one dose (typically two doses) is particularly useful in immunologically naïve patients e.g. for people who have never received an influenza vaccine before, or for vaccines including a new HA subtype. Multiple doses will typically be administered at least 1 week apart (e.g. about 7 weeks, about 3 weeks, about 4 weeks, about 6 weeks, about 8 weeks, about 12 weeks, about 16 weeks, etc.).

Vaccines produced by the invention may be administered to patients at substantially the same time as (e.g. during the same medical consultation or visa to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5 (acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step or mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a cell substrate is used for reassortment or reverse genetics procedures, or for viral growth, it is preferably one that has been approved for use in human vaccine production e.g. as in Ph Eur general chapter 5.2.3.

MODES FOR CARRYING OUT THE INVENTION 595 patients (male & female children, 6 to <36 months) are split into 17 groups of 35 each. Each of the groups receives either trivalent (A/H1N1, A/H3N2, B) or tetravalent (A/H1N1, A/H3N2, B/Victoria, B/Yamagata) influenza vaccine. The vaccine is administered either as a 0.5 mL volume (15 µg/dose/strain, 45 µg or 60 µg in total) or as a 0.25 mL volume (7.5 µg/dose/strain; 22.5 µg or 30 µg in total). One of the groups receives an pediatric dose of an existing marketed trivalent inactivated vaccine. The vaccine is given by intramuscular injection and is supplied either in pre-filled syringes or in vials. Three different adjuvant quantities (achieved by dilution) are tested.

The trivalent vaccine includes influenza strains as recommended for the influenza season 2005-2009 in the Northern Hemisphere: A/Brisbane/59/2007-like, A/Brisbane/10/2007-like virus, and B/Florida/4/2006-like. The B/Florida/4/2006-like virus is in the B/Yamagata lineage, so the tetravalent vaccine additionally included antigen from B/Malaysia/2506/2004-like virus, which is in the B/Victoria lineage.

Subjects receive two doses of vaccine at days 1 and 29 (except for two groups, who receive a single dose at day 1) and influenza-specific immune responses are assessed by analyzing blood collected at baseline (prior to vaccination), at day 28 and at day 50. Serum samples are assessed by strain-specific hemagglutination inhibition (HI) assays against influenza strains A/H1N1, A/H3N2 and B, including homologous and heterovariant strains.

Thus the 17 groups are as follows:

| Group | H1N1 (µg) | H3N2 (µg) | B/Yam (µg) | B/Vic (µg) | Squalene (µg) | Number of doses | Dose (mL) |
|---|---|---|---|---|---|---|---|
| A | 7.5 | 7.5 | 7.5 | — | — | 2 | 0.25 |
| B | 15 | 15 | 15 | — | — | 2 | 0.5 |
| C | 7.5 | 7.5 | 7.5 | 7.5 | — | 2 | 0.25 |
| D | 15 | 15 | 15 | 15 | — | 2 | 0.5 |
| E | 7.5 | 7.5 | 7.5 | — | 1.22 | 2 | 0.25 |
| F | 7.5 | 7.5 | 7.5 | 7.5 | 1.22 | 2 | 0.25 |
| G | 7.5 | 7.5 | 7.5 | — | 2.44 | 2 | 0.25 |
| H | 15 | 15 | 15 | — | 2.44 | 2 | 0.5 |
| I | 7.5 | 7.5 | 7.5 | 7.5 | 2.44 | 2 | 0.25 |
| J | 15 | 15 | 15 | 15 | 2.44 | 2 | 0.5 |
| K | 7.5 | 7.5 | 7.5 | — | 4.88 | 2 | 0.25 |
| L | 15 | 15 | 15 | — | 4.88 | 2 | 0.5 |
| M | 7.5 | 7.5 | 7.5 | 7.5 | 4.88 | 2 | 0.25 |
| N | 15 | 15 | 15 | 15 | 4.88 | 2 | 0.5 |
| O | 15 | 15 | 15 | — | 9.75 | 1 | 0.5 |
| P | 15 | 15 | 15 | 15 | 9.75 | 1 | 0.5 |
| Q | 7.5 | 7.5 | 7.5 | — | — | 2 | 0.25 |

In a further study, 357 patients (male & female, >65 years old) are spilt into 8 groups. Each of the groups receives a trivalent influenza vaccine (A/H1N1, A/H3N2, B) by intramuscular injection (0.5 mL), with or without a squalene-in-water emulsion. The vaccine is supplied in pre-filled syringes. Three different adjuvant quantities (achieved by dilution) are tested.

The influenza strains are as recommended for the influenza season 2008-2009 in the Northern Hemisphere: A/Brisbane/59/2007-like, A/Brisbane/10/2007-like virus, and B/Florida/4/2006-like.

Subjects receive a single dose and influenza-specific immune responses are assessed by analyzing blood collected at baseline (prior to vaccination), at 7 days (Day 8), and at 21 days (Day 22) after vaccination. Serum samples are assessed by strain-specific hemagglutination inhibition (HI) assays against influenza strains A/H1N1, A/H3N2 and B. Cell-mediated immunity assays are also performed.

Thus the eight groups are as follows:

| Group | H1N1 (µg) | H3N2 (µg) | B (µg) | Squalene (mg) | Dose (mL) |
|---|---|---|---|---|---|
| A | 15 | 15 | 15 | — | 0.5 |
| B | 15 | 30 | 15 | — | 0.5 |
| C | 15 | 15 | 15 | 2.44 | 0.5 |
| D | 15 | 30 | 15 | 2.44 | 0.5 |
| E | 15 | 15 | 15 | 4.88 | 6.5 |
| F | 15 | 30 | 15 | 4.88 | 0.5 |
| G | 15 | 15 | 15 | 9.75 | 0.5 |
| H | 15 | 30 | 14 | 9.75 | 0.5 |

For both influenza A strains, all three CHMP criteria are met in patient groups C-H (i.e. the adjuvanted vaccines).

For the influenza B strain, all three CHMP criteria are met in the groups which receive 4.88 mg squalene or 9.75 mg squalene. In the group which receives the unadjuvanted vaccine, only one of the CHMP criteria is met, but in the group which receives 2.44 mg squalene two of the three CHMP criteria are met.

Thus, even a low dose of squalene in the vaccine can increase the immune protection against influenza A and B strains.

It will be understood that the invention has been described by way of example only and modifications may be made whilst remaining within the scope and spirit of the invention.

REFERENCES

[1] Minutello et al. (1999) *Vaccine* 17:99-104.
[2] WO2007/052155.
[3] WO2008/043774.
[4] WO02/28422.
[5] WO02/067983.
[6] WO02/074336.
[7] WO01/21151.
[8] WO02/097072.
[8] WO02/005/113756.
[10] Huckriede et al. (2003) *Methods Enzymol* 373; 74-91.
[11] Saito et al. (2004) *J Med Virol* 74(2):336-43.
[12] Hoffmann et al. (2002) *Vaccine* 20:3165-3170.
[13] Subbarao et al. (2003) *Virology* 305:192-200.
[14] Liu et al (2003) *Virology* 314:580-590.
[15] Ozaki et al. (2004) *J. Virol.* 78:1851-1857.
[16] Webby et al. (2004) *Lancet* 363:1099-1103.
[17] WO00/60050.
[18] WO01/04333.
[19] U.S. Pat. No. 6,649,372.
[20] Neumann et al. (2005) *Proc. Natl Acad Sci USA* 102:16825-9.
[21] WO2006/067211.
[22] WO01/83794.
[23] Hoffmann et al. (2000) *Virology* 267(2):310-7.
[24] Herlocher et al. (2004) *J Infect Dis* 190(9): 1627-30.
[25] Le et al. (2005) *Nature* 437(7062): 1108.
[26] Gambaryan & Matrosovich (1992) *J Virol Methods* 39(1-2):111-23.
[27] Mastrosovich et al (1999) *J Virol* 73: 1146-55.
[28] Stevens et al. (2006) *J Mol Biol* 355:1143-55.
[29] Couceiro & Banm (1994) *Mem Inst Oswaldo Cruz* 89(4):587-91.
[30] WO2008/068631.
[31] Rota et al. (1992) *J Gen Virol* 73:2737-42.
[32] GenBank sequence GI:325176.
[33] McCullers et al. (1999) *J Virol* 73:7343-8.
[34] GenBank sequence GI:325237.
[35] Treanor et al. (1990) *J Infect Dis* 173:1467-70
[36] Keitel et al. (1996) *Clin Diagn Lab Immunol* 3:507-10.
[37] Kistner et al. (1998) *Vaccine* 16:960-8.
[38] Kistner et al. (1999) *Deb Biol Stand* 98:101-110.
[39] Bruhl et al. (2000) *Vaccine* 19:1149-58.
[40] Pan et al. (2001) *Vaccine* 19:2716-21.
[41] http://www.atcc.org/
[42] http://locus.umdnj.edu/
[43] WO03/076601.
[44] WO2005/042728.
[45] WO03/043415.
[46] WO01/85938.
[47] WO2006/108846.
[48] WO97/37000.
[49] Brands et al. (1999) *Dev Biol Stand* 98:93-100.
[50] Halperin et al. (2002) *Vaccine* 20:1240-7.
[51] Tree et al. (2001) *Vaccine* 19:3444-50.
[52] EP-A-1260581 (WO01/64846).
[53] WO2006/071563.
[54] WO2005/113758.
[55] WO97/37001.
[56] WO2006/027698.
[57] EP-B-0870508.
[58] U.S. Pat. No. 5,948,410.
[59] Lundblad (2001) *Biotechnology and Applied Biochemistry* 34:195-197.
[60] *Guidance/or Industry: Bioanalytical Method Validation*, U.S. Department of Health and Human Services Food and Drag Administration Center for Drug Evaluation and Research (CDER) Center for Veterinary Medicine (CVM). May 2001.
[61] Ji et al. (2002) *Biotechniques*, 32:1162-7.
[62] Briggs (1991) *J Parenter Sci Technol* 45:7-12.
[63] Lahijani et al. (1998) *Hum Gene Ther.* 9:1173-80.
[64] Lokteff et al. (2001) *Biologicals.* 29:123-32.
[65] Gennaro (2000) Remington: *The Science and Practice of Pharmacy.* 20th edition, ISBN: 0683306472.
[66] Banzhoff (2000) *Immunology Letters* 71:91-96.
[67] O'Hagan (2007) *Expert Rev Vaccines.* 6(5):699-710.
[68] Bernstein et al. (2008) *J Infect Dis.* 197(5):667-75.
[69] Stephenson et al. (2005) *J Infect Dis.* 191(8): 1210-5.
[70] Han et al. (2005) *Impact of Vitamin E on Immune Function end Infectious Diseases in the Aged at Nutrition, Immune functions and Health* EuroConference, Paris, 9-10 Jun. 2005.
[71] U.S. Pat. No. 6,630,161.
[72] WO90/14837.
[73] Podda & Dei Giudice (2003) *Expert Rev Vaccines* 2:197-203.
[74] Podda (2001) *Vaccine* 19: 2673-2680.
[75] *Vaccine Design: The Subunit and Adjuvant Approach* (eds. Powell & Newman) Plenum Press 1995 (ISBN 0-306-44867-X).
[76] *Vaccine Adjuvants; Preparation Methods end Research Protocols* (Volume 42 of *Methods in Molecular Medicine* series). ISBN: 1-59259-083-7. Ed. O'Hagan.
[77] Allison & Byers (1992) *Res Immunol* 14.3:519-25.
[78] Hariharon et al. (1995) *Cancer Res* 55:3486-9.
[79] US-2007/0014805.
[80] US-2007/0191314.
[81] Suli et al. (2004) *Vaccine* 22(25-26):3464-9.
[82] WO95/11700.
[83] U.S. Pat. No. 6,080,725.
[84] WO2005/097181.
[85] WO2006/113373.

[86] Potter & Oxford (1979; *Br Med Bull* 35: 69-75.
[87] Halperin et al. (1979) *Am J Public Health* 69:1247-50.
[88] Herbert et al. (1979) *J Inject Dis* 140:234-8.
[89] Greenbaum et al. (2004) *Vaccine* 22:2566-77.
[90] Zurbriggen et al. (2003) *Expert Rev Vaccines* 2:295-304.
[91] Piascik (2003) *J Am Pharm Assoc* (Wash D.C.). 43:728-30.
[92] Mann et al. (2004) *Vaccine* 22:2425-9.
[93] Chen et al. (2003) *Vaccine* 21:2830-6.

What is claimed:

1. An influenza virus vaccine for raising an immune response in a patient of 6 to <36 months of age comprising: (i) hemagglutinin from at least two influenza A virus strains and at least two influenza B virus strains wherein the concentration of hemagglutinin per strain is at least 25 μg/mL; and (ii) an oil-in-water emulsion adjuvant with submicron oil droplets, comprising squalene, where the squalene concentration is ≤10 mg/mL and the minimum amount of squalene per dose is 0.5 mg, and wherein the influenza B virus strains include a B/Victoria/2/87-like influenza B virus strain and a B/Yamagata/16/88-like influenza B virus strain, and wherein the vaccine has a unit dose volume of 0.5 mL;
wherein the hemagglutinin is in the form of split virions, or purified surface antigens.

2. The vaccine of claim 1, wherein the vaccine:
(a) comprises hemagglutinin from (i) a H1N1 influenza A virus strain; (ii) a H3N2 influenza A virus strain; (iii) a B/Victoria/2/87-like influenza B virus strain; and (iv) a B/Yamagata/16/88-like influenza B virus strain; and/or
(b) wherein the ratio of squalene to hemagglutinin in the vaccine is 42:1.

3. The vaccine of claim 1, wherein the vaccine is:
(a) a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain, a squalene concentration of 9.75 mg/mL, and a unit dosage volume of 0.5 mL; or
(b) a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain, a squalene concentration of 4.88 mg/mL, and a unit dosage volume of 0.5 mL.

4. An influenza virus vaccine for raising an immune response in a patient of 6 to <36 months of age comprising: (i) hemagglutinin from at least two influenza A virus strains and at least two influenza B virus strains wherein the concentration of hemagglutinin per strain is at least 25 μg/mL; and (ii) an oil-in-water emulsion adjuvant with submicron oil droplets, comprising squalene, where the squalene concentration is ≤10 mg/mL and the amount of squalene per dose is 2.4 or 1.2 mg, and wherein the influenza B virus strains include a B/Victoria/2/87-like influenza B virus strain and a B/Yamagata/16/88-like influenza B virus strain, and wherein the vaccine has a unit dose volume of 0.2-0.3 mL.

5. The vaccine of claim 4, wherein the hemagglutinin is in the form of split virions, or purified surface antigens.

6. The vaccine of claim 4, wherein the vaccine has a unit dose volume of 0.25 mL.

7. The vaccine of claim 4, wherein the vaccine is:
(a) a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain and a squalene concentration of 9.75 mg/mL; or
(b) a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain and a squalene concentration of 4.88 mg/mL.

8. An influenza virus vaccine for raising an immune response in a patient of 6 to <36 months of age comprising: (i) hemagglutinin from at least two influenza A virus strains and at least two influenza B virus strains wherein the concentration of hemagglutinin per strain is at least 25 μg/mL; and (ii) an oil-in-water emulsion adjuvant with submicron oil droplets, comprising squalene, where the amount of squalene per dose is 2.4 or 1.2 mg, and wherein the influenza B virus strains include a B/Victoria/2/87-like influenza B virus strain and a B/Yamagata/16/88-like influenza B virus strain, and wherein the vaccine has a unit dose volume of 0.25 mL.

9. The vaccine of claim 8, wherein the hemagglutinin is in the form of split virions, or purified surface antigens.

10. The vaccine of claim 8, wherein the vaccine is:
(a) a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain and a squalene concentration of 9.75 mg/mL; or
(b) a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain and a squalene concentration of 4.88 mg/mL.

11. The vaccine of claim 1, wherein the vaccine is to be administered in more than one dose.

12. The vaccine of claim 4, wherein the vaccine is to be administered in more than one dose.

13. The vaccine of claim 8, wherein the vaccine is to be administered in more than one dose.

14. The vaccine of claim 1, wherein the hemagglutinin is in the form of split virions.

15. The vaccine of claim 4, wherein the hemagglutinin is in the form of split virions.

16. The vaccine of claim 8, wherein the hemagglutinin is in the form of split virions.

17. The vaccine of claim 1, wherein the hemagglutinin is in the form of purified surface antigens.

18. The vaccine of claim 4, wherein the hemagglutinin is in the form of purified surface antigens.

19. The vaccine of claim 8, wherein the hemagglutinin is in the form of purified surface antigens.

20. The vaccine of claim 1, wherein the vaccine is a tetravalent inactivated influenza vaccine with a A/H1N1 strain, a A/H3N2 strain, an influenza B virus strain in the B/Yamagata lineage, and an influenza B virus strain in the B/Victoria lineage, having a hemagglutinin concentration of 30 μg/mL per strain, a squalene concentration of 9.75 mg/mL, and a unit dosage volume of 0.5 mL.

* * * * *